US005859308A

United States Patent [19]
Mirochnitchenko et al.

[11] Patent Number: 5,859,308
[45] Date of Patent: Jan. 12, 1999

[54] TRANSGENIC ANIMALS AND RELATED ASPECTS

[75] Inventors: Oleg Mirochnitchenko, Highland Park; Masayori Inouye, Bridgewater, both of N.J.

[73] Assignee: University of Medicine and Denistry of New Jersey, Newark, N.J.

[21] Appl. No.: 365,966

[22] Filed: Dec. 29, 1994

[51] Int. Cl.$^6$ ............................ C12N 5/06; A01K 67/027
[52] U.S. Cl. ........................ 800/2; 435/172.1; 435/172.3; 435/240.2; 435/320.1; 800/DIG. 1; 935/6; 935/14; 935/22; 935/33; 935/70
[58] Field of Search ............................. 435/172.1, 172.3, 435/240.2, 320.1; 800/2, DIG. 1; 935/6, 14, 22, 33, 34, 70

[56] References Cited

U.S. PATENT DOCUMENTS

| | | | |
|---|---|---|---|
| 4,736,866 | 4/1988 | Leder et al. | 800/2 |
| 5,089,408 | 2/1992 | Akasaka et al. | 435/192 |
| 5,175,383 | 12/1992 | Leder et al. | 800/2 |
| 5,175,384 | 12/1992 | Krimpenfort et al. | 800/2 |
| 5,175,385 | 12/1992 | Wagner et al. | 800/2 |
| 5,179,017 | 1/1993 | Axel et al. | 435/240.2 |

FOREIGN PATENT DOCUMENTS

| | | |
|---|---|---|
| 89306071 | 5/1993 | European Pat. Off. . |
| WO8807541 | 10/1988 | WIPO . |

OTHER PUBLICATIONS

Akasaka, M., Mizoguch, J., Yoshimura, S., and Watanabe, K., "Nucleotide sequence of cDNA for rabbit glutathione peroxidase", 17(5):2136 (1989).

Benedetto, M. T., Yuzuru, A., and Gordon, J. W., Isolation and analysis of the mouse genomic sequence encoding $Cu^{2+}$–$Zn^{2+}$ superoxide dismutase, *Gene*, 99:191–194 (1991).

Bewley, G. C., "cDNA and deduced amino acid sequence of murine Cu–Zu superoxide dismutase", *Nucleic Acids Research*, 16(6):2728 (1988).

Big Blue™ Mouse Mutagenesis Assay System, Stratagene, Cincinnati, Ohio.

Ceballos, I., et al., "Expression of Human Cu–Zn superoxide dismutase gene in transgenic mice: Model for Gene dosage effect in down syndrome" *Free Rad. Res. Commis.*, vols. 12–13, pp. 581–589 (1991).

Ceballos–Picot, I., et al., "Age–related changes in antioxidant enzymes and lipid peroxidation in brains of control and transgenic mice overexpressing copper–zinc superoxide distmutase", *Mutation Research*, 275:281–293 (1992).

Chan, P.H., et al., "Cold–induced Brain Edema and Infarction are Reduced in Transgenic Mice Overexpressing CuZn–Superoxide Dismutase", *Annals. of Neurology*, 29(5):482–487 (1991).

Chen, T., Richi, J. P. Jr., Lang, C. A., "Life Span Profiles of Glutathione and Acetaminophen Detoxification", *Drug Metabolism and Dispositions*, 18(6):882–887.

Epstein, Charles J., et al., "Transgenic mice with increased Cu/Zn–super–Oxide dismutase activity: Animal model of dosage effects in Down syndrome", *Proc. Natl. Acad. Sci. USA*, 84:8044–8048 (1987).

Gautier, C., Mehtali, M., and Lathe, R., "A ubiquitous mammalian expression vector, pHMG, based on a housekeeping gene promoter", *Nucleic Acids Research*, 17(20):8389 (1989).

Ho, Y. S., Howard, A. J., and Crapo, J. D., "Nucleotide sequence of a rat glutathione peroxidase cDNA", *Nucleic Acid Research*, 16(11):5207 (1988).

Ho, Y.S., and Crapo, J. D., "cDNA and deduced amino acid sequence of rat copper–zinc–containing superoxide dismutase", *Nucleic Acid Research*, 15(16):6746 (1987).

Kolb, e., Laine, E., Strehler, D., & Staehel, P., "Resistance to Influenza virus Infection of mx Transgenic Mice Expressing Mx Protein under the Control of Two Constitutive Promoters", *J. of Virology*, p. 1709–1716, Mar. 1992.

Lerch, Konrad and Ammer, Doris, "Amino Acid Sequence of Copper–Zinc Superoxide Dismutase from Horse Liver", *The Journal of Biological Chemistry*, 256(22):11545–11551 (1981).

Lopez–Torres, M., Perez–Campo, R., Rojas, C., Cadenas, S., and Barja, G., "Simultaneous Induction of SOD, Glutathione Reductase, GSH, and Ascorbate in Liver and Kidney Correlates with Survival During Aging", *Free Radical Biol. & Med.* 15: 133–142 (Received 21 May 1992; Revised 3 Feb. 1993; Accepted 24 Feb. 1993).

Mirault, M. E., Tremblay, A., Beaudoin, N., and Tremblay M., "Overexpression of Seleno–glutathione Peroxidase by Gene Transfer Enhances the Resistance of T47D Human Breast Cells to Clastogenic Oxidants", *The Journal of Biological Chemistry*, 266(31):20752–20760 (1991).

Mirault, M. E., Tremblay, A., Trepanier, G., Furling, D., and Puymirat, J., "Transgenic Mice Overexpressing Se Glutathione Peroxidase in the Brain: Differential Resistance to MPTP Mediated Neurotoxicity", *J. Cellular Biochem.*, Keystone Symposia on Molecular and Cellular Biology, Supp. 17, Molecular Biology of Aging, p. 168 (1993).

Sherman, L., Dafni, N., Lieman–Hurwitz, J., and Groner, Y., "Nucleotide sequence and expression of human chromsome 21–encoded superoxide dismutase mRNA", *Proc. Natl. Acad. Sci. USA*, 80:5465–5469 (1983).

(List continued on next page.)

*Primary Examiner*—Christopher S. F. Low
*Attorney, Agent, or Firm*—Weiser & Associates, P.C.

[57] ABSTRACT

A transgenic animal, the genome of which comprises a transgene for superoxide dismutase (SOD), erythrocyte-glutathione peroxidase (GPE), or plasma-glutathione peroxidase (GPP), is disclosed. A double transgenic animal comprising the transgenes for both SOD and GPE is also disclosed. Methods for making the transgenic animals are disclosed. Both the SOD gene and the two GP genes code for proteins which control the level of reactive oxidative species (ROS) which accumulate in cells as a result of metabolism. Cell lines from both SOD and GP transgenic animals and methods for use of the transgenic animals as models are also disclosed.

9 Claims, 9 Drawing Sheets

OTHER PUBLICATIONS

Steinman, H. M., Naik, V. R., Abernethy, J. L., and Hill, R. L., "Bovine Erythrocyte Superoxide Dismutase", *The Jounral of Biological Chemistry*, 249(22):7326–7333 (1974).

Sukenaga, Y., Ishida, K., Takeda, T., and Takagi, K., "cDNA sequence coding for human glutathione peroxidase", *Nucleic Acids Research*, 15(17):7178 (1987).

Takahashi, K., Avissar, N., Whitin, J., Cohen, H., "Purification and Characterization of Human Plasma Glutathione Peroxidase: A Selenoglycoprotein Distinct from the Known Cellular Enzyme", *Archives of Biochemistry and Biophysics*, 256(2):667–686 (1987).

Takahashi, K., Akasaka, M., Yamamoto, Y., Kobayashi, C., Mizoguchi, J., and Koyama, Jiro, "Primary Structure of Human Plasma Glutathione Peroxidase Deduced from cDNA Sequences", *J. Biochem.*, 108:145–148 (1990).

Weisbrot, M., Miroshnichenko, O., and Inouye, M., "Acetaminophen Toxicity in Transgenic Mice Overexpressing Human Glutathione Peroxidase", Poster Presentation, 10th International Medical Sciences Student Congress, Istanbul, May 4–7, 1994.

White, Carl W., "Transgenic Mice with Expression of Elevated Levels of Copper–Zinc Superoxide Dismutase in the Lungs are Resistant to Pulmonary Oxygen Toxicity", *The American Society for Clinical Investigation, Inc.*, 87:2162–2168 (1991).

Yarom, R., Sapoznikov, D., Havivi, Y., Avraham, K.B., Shickler, M., and Groner, Y., "Premature Aging Changes in Neuromuscular Junctions of Trans genic Mice with an Extra human CuZn–SOD Gene: A Model for Tongue Pathology in Down's Syndrome", *J. Neurol. Sci.* 88:41–53 (1988).

Omar et al. 1987, Cancer Research 47: 3473–3476.

FIG. 7A
FIG. 7B
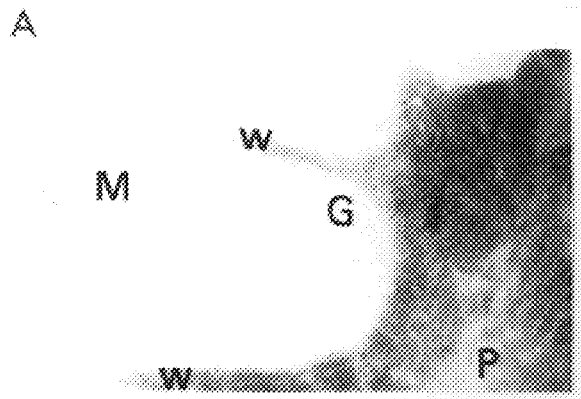
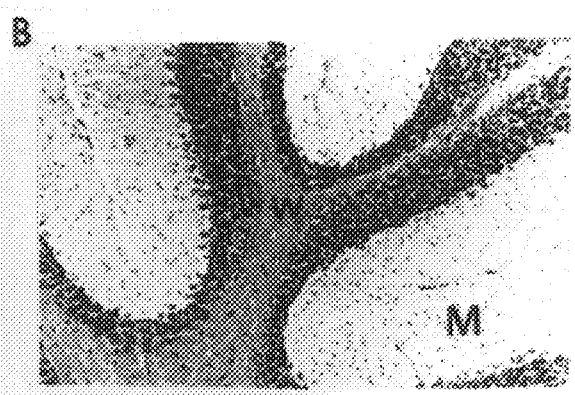
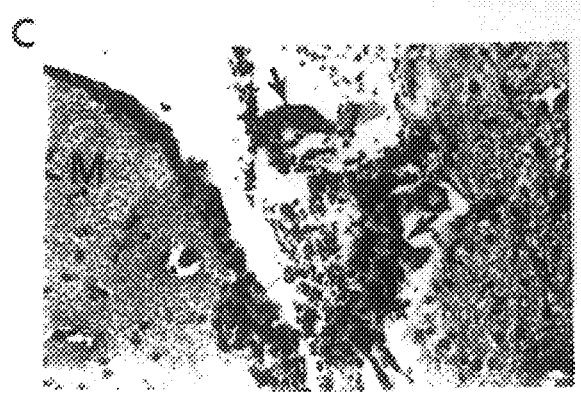
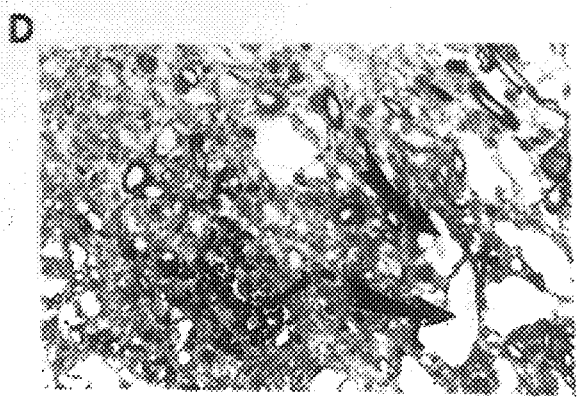
FIG. 7C
FIG. 7D

TRANSGENIC ANIMALS AND RELATED ASPECTS

FIELD OF THE INVENTION

This invention relates to transgenic animals. The invention relates further to animals whose genotype and phenotype have been modified so that the transgenic animals show different properties than the non-transgenic animals. The invention deals with the control and the relief of the symptoms of stress.

BACKGROUND OF THE INVENTION

The human body depends on oxygen in order to live. In fact, virtually all life on our planet requires oxygen. Unfortunately, when oxygen is used intracellularly to fuel the aerobic chemical processes required for life, toxic oxidative by-products, referred to as reactive oxidative species (ROS) are left behind in the cell.

The body has three major enzymes which detoxify ROS. These enzymes are superoxide dismutase (SOD), which catalyzes the transformation of the superoxide anion to peroxide; catalase, which catalyzes the transformation of hydrogen peroxide into water; and glutathione peroxidase ("GP"), which catalyzes the destruction of hydrogen and lipid peroxides, using glutathione as an electron donor. GP occurs in various forms, the most significant of which are plasma GP ("GPP") and erythrocyte GP ("GPE"). Of the three antioxidant enzymes, SOD and GP are the most important.

The presence and the activity of these enzymes play a critical role in human health. Primarily, the balance between the components of the antioxidant defenses appears to be of prime importance for the cellular resistance to what is called "oxidative stress", that is, the intracellular imbalance between prooxidants causing release of ROS during metabolism and antioxidants which destroy the ROS.

The invention has several embodiments. Broadly considered, the invention deals with the control, or the treatment of stress, and under certain circumstances described herein, the alleviation of the symptoms of stress. The invention in one of its very interesting applications addresses the universal problem of mortal animals and human beings, the problem of aging. For this purpose, the invention provides a transgenic non-human animal which produces or overproduces SOD and/or GP. These transgenic animals are an ideal, useful model to evaluate and/or monitor in a practical manner the effect of SOD and/or GP when these transgene animals are subjected to various stressful conditions, such as the diseases discussed herein and/or on the aging phenomena.

Several theories have been postulated to explain why cells age and ultimately die. Until relatively recently, many scientists subscribed to the theory of a genetic basis for senescence. Since the removal of the elders from a population would reduce the drain on resources and so allow the younger individuals freer access to those resources, it was felt that aging was programmed in genes whose sole function is to cause senescence in the organism. This theory has lost favor, however, because wild animals usually do not survive long enough in the wild to become senescent. Additionally, until recently, human life expectancy was not the 75 years experienced in today's industrial societies, but was less than 40 years.

Today, it is widely believed that aging results from repeated minute damage to cells which accumulates over time, causing loss of cellular function. This damage is due to ROS released as a result of the use of oxygen for energy metabolism.

According to this theory, ROS made up of free radicals and highly oxidative compounds are generated during metabolism.

These ROS, such as superoxide ($O_2^-$), peroxide ($H_2O_2$), and hydroxyl radical ($OH^-$), are highly toxic and cause serious damage to various cellular components, such as chromatin, structural macromolecules, cellular and organelle membranes, and other components. Therefore, in order to protect itself, organisms have developed defense mechanisms to remove these toxic ROS.

Several diseases in humans have been associated with an imbalance of the antioxidant defense system with an increased or decreased SOD expression relative to GP expression. Examples of such diseases include Alzheimer's Disease, Down's Syndrome, amyotrophic lateral sclerosis, and Parkinson's Disease.

There is convincing evidence that prolonged oxidative stress plays an important role in carcinogenesis. It is believed that ROS cause mutations in DNA which may ultimately lead to cancer.

Results of several studies indicate that an increase or a decrease in activity of one of the antioxidant enzymes without concomitant change in activity of the other may lead to the prooxidant state within the cell and could contribute to the aging phenomenon and to various disease processes. For example, an increase in SOD activity would lead to the increased production of peroxide, a potent prooxidant. Since GP acts to detoxify peroxide, inadequate supplies of GP to deal with the increased peroxide load due to increased SOD activity, can cause an increase in cellular damage.

It is evident that an imbalance of the detoxifying enzymes has adverse effects on the mammal and that it will be very desirable to control and properly balance the role and effect of the principal antioxidant enzymes.

In addition, the modes of action of several toxic substances involve the production, overproduction or depletion of reactive oxidative species. For example, benzidine, a pollutant present in automobile emissions, has been shown to cause increased levels of ROS. Another poison, benzene, a common industrial pollutant, causes increased production of ROS in vitro. The increase in ROS associated with benzene is believed to be the cause of benzene's toxicity. A third example is that of acetaminophen, a harmless and useful analgesic when taken at therapeutic levels. At toxic levels, however, acetaminophen causes depletion of GP from the liver, resulting in liver damage.

An intriguing aspect of the role of antioxidants is the sensitivity of cells to hyperthermia, often leading to death of the cell. In hyperthermic cells, levels of hydrogen peroxide build up rapidly due to the increased rate of metabolism due to the increased temperature. High levels of hydrogen peroxide are thought to function as a signal to the cell to make heat protective proteins. Tumor cells have increased levels of GP and are more sensitive to hyperthermia than are normal cells. It is believed that the high levels of GP in tumor cells leads to depletion of hydrogen peroxide so that heat protective proteins are not made, thus rendering the cell more sensitive to hyperthermia.

It is evident from this review that the literature reports often contradicting or inconclusive results that do not provide guidance as to how to control ROS species in mammals in a reliable and reproducible manner. Further, the literature provides often contradicting and inconclusive results of the effects or changes in the production of ROS in mammals.

Significantly, no report has been found of a double transgenic animal bearing the genes for both SOD and GP. Such a transgenic animal is an ideal practical model to determine the effects of disruptions of the balance between the two enzymes due to time, environmental conditions and/or various agents, a balance that has been shown to be crucial in preventing cell damage due to ROS. The double transfgenic animal would also contribute to the elucidation of many of the mysteries of aging.

BRIEF DESCRIPTION OF THE DRAWINGS

FIGS. 7A–7D are a series of microphotographs showing the cerebellar hemorrhage in brains of transgenic mice as compared to controls.

DEPOSITS

Figure 1A:
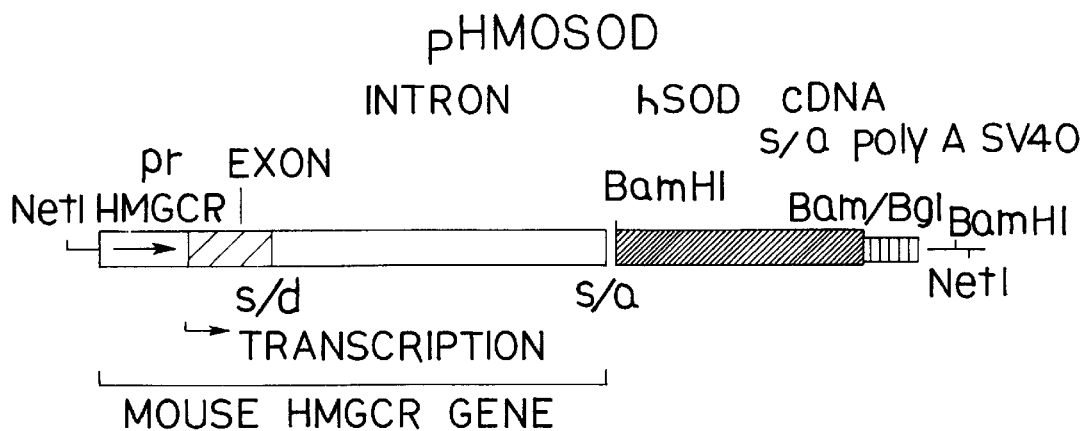
FIG. 1A is a diagram showing the structure of the human Cu,Zn SOD transgene.
Figure 1B:
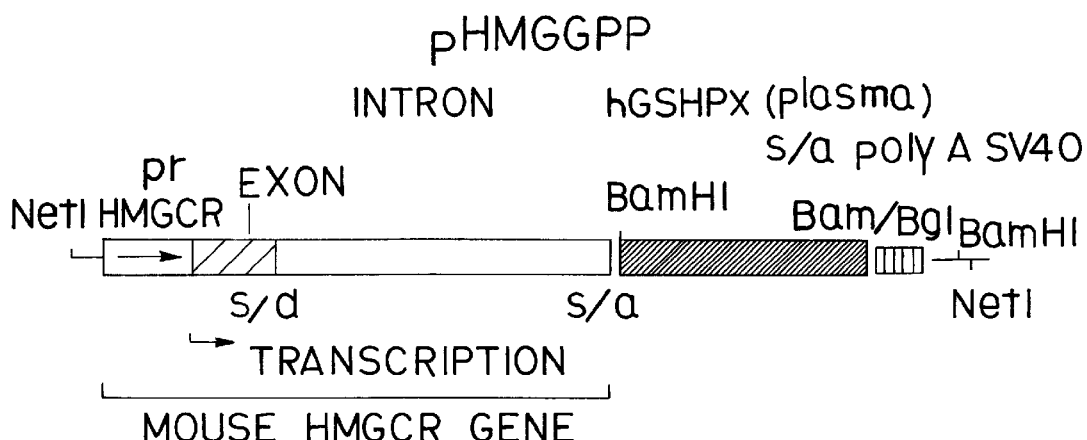
FIG. 1B is a diagram showing the structure of the human plasma GP transgene.
Figure 1C:
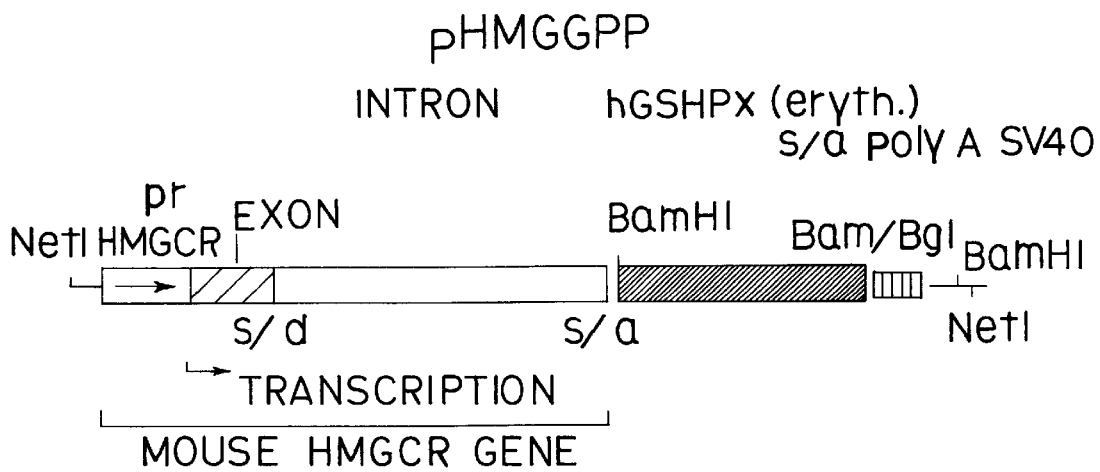
FIG. 1C is a diagram showing the structure of the human erythrocyte GP transgene.

Plasmids bearing the fusion genes shown in FIG. 1 have been deposited in the American Type Culture Collection, Rockville, Md., pHMGSOD has been given ATCC Accession Number 69697; pHMGGPP has been given ATCC Accession Number 69698; and pHMGGPE has been given ATCC Accession Number 69696; all on Sep. 29, 1994.

SUMMARY OF SEVERAL EMBODIMENTS OF THE INVENTION

The best mode of the invention will be described hereinafter with particular reference to a transgenic mouse.

This invention relates to the production of transgenic non-human animals whose somatic and germ cells comprise and express transgenes coding for glutathione peroxidase (GP), for Cu,Zn superoxide dismutase (SOD), and for both GP and SOD. The transgenic animals overexpress the enzymes ubiquitously in all tissues in varying amounts. The transgenic mice of this invention will generally contain all other enzyme systems normally found in the body, including catalase. The transgenic mice of the invention may carry additional transgenes for other antioxidant enzymes, such as catalase. The tralisgenes of this invention are transferred to succeeding generations.

The invention also provides a method for controlling and alleviating the symptoms of an increase in ROS.

The intention also relates to vectors for transferring the transgenes into the genome of a non-human animal. A vector for introducing the SOD transgene into the animals comprises the gene coding for SOD, together with a promoter generally other than the indigenous promoter for SOD operably linked to the SOD gene. Vectors for introducing the GP gene in both the erythrocyte GP form (GPE) and the plasma GP form (GPP) of the enzymes also are provided by this invention. The vectors for introducing GP into the genome of the transgenic animals comprise a gene coding for GPE and for GPP, respectively.

The vectors for introducing GP into the genome of transgenic animals further comprises a promoter operably linked to the GP gene other than the indigenous promoters for GPE and GPP, respectively. The promoter operably linked to the SOD and GP transgenes may be what is called a "luxury" promoter, but generally it is a constitutive or "housekeeping" promoter, and may be derived from a non-human species source.

An example of such a non-human housekeeping promoter is murine hydroxy-methylglutaryl-Coenzyme A reductase (mHMGCR). HMGCR, being a housekeeping gene promoter, is highly conserved between species and is expressed in all cell types. Non-specific expression is favored over tissue-specific expression by using such a housekeeping gene promoter.

The invention also provides the process of making the transgenic animals containing SOD, GPE, GPP, and both SOD and GPE, respectively, operably linked to a non-human, housekeeping promoter, such as, for example, mHMGCR.

Additionally, the invention provides transgenic animals, like mice, with a phenotype characterized by increased sensitivity to hyperthermia. In one embodiment, the transgenic animal with a phenotype characterized by increased sensitivity to hyperthermia contains with its genome the transgene for GPE, another transgene is that for GPP.

The invention also relates to transgenic animals, like mice, whose germ cells and somatic cells contain and express recombinant genes coding for SOD, GPE, GPP and both SOD and GPE or GPP, operably linked to an appropriate promoter, such as a housekeeping promoter.

In a particular embodiment, the invention relates to a mammal, like a mouse, which carries both the GP and SOD genes and coexpresses both enzymes, that will be able to metabolize ROS more effectively and generating less or without generating products, like ROS harmful to the mammal. The concurrent or overlapping balanced and controlled over-expression of both antioxidant enzymes provides a powerful animal model of great practical interest. A typical animal is a mouse, whose germ cells and somatic cells contain and express recombinant genes encoding both SOD and GPE or GPP, especially human GPE (hGPE), human GPP (hGPP) and human SOD (hSOD). The transgene exhibits a combination of unique properties, like decreased sensitivity to stress like hyperthermia. Such transgene mammal is expected to show a longer life span as compared to a control or "normal" mammal. The implications of this observation are of major importance.

The invention also provides a cell line comprising cells derived from the SOD, GP, or SOD and GP transgenic animal of the invention. These cell lines comprise the transgene of the transgenic animal and can be used to determine the effects of overexpression of the genes coded for by the transgenes on a cellular level.

The invention also provides transgenic animals, like mice, with a phenotype characterized by increased rates of mutagenesis following exposure to carcinogens. In one embodiment, the transgenic animal with a phenotype characterized by increased rates of mutagenesis following exposure to carcinogens contains within its genome the transgene for SOD operably linked to a housekeeping promoter.

The invention also relates to recombinant genes which are substantially homologous with the naturally occurring genes SOD, GPE, GPP especially the human species, to express the corresponding enzymes that are functionally equivalent in terms of catalyzing the known reactions of these respective enzymes.

The animals of the invention may be used to monitor ambient levels of compounds, such as benzidine or benzene, which are known to affect ROS. The presence and level of these compounds in the workplace can be tested by exposing the animals to such compounds and to periodically assay the levels of ROS in the animals' tissues. In this way, the animals will be used as monitors of the work environment. Because these animals are more susceptible to the ROS forming effects of such compounds than are humans or nontransgenic animals, the transgenic animals of the invention will function like the proverbial "canary in a coal mine" to warn of higher than safe levels of these pollutants. It will also be possible to modify such compounds to decrease their capability of generating ROS or to synthesize antagonists to neutralize the adverse effect of such compounds.

The transgenic animals of the invention will be found useful as models to evaluate various diseases that are due, at least in part, to an imbalance of the oxidative status of the human body. Such diseases include, but are not limited to, Alzheimer's disease, Downs syndrome, amyotrophic lateral sclerosis, Parkinson's Disease, and other clinical conditions in which oxygen radicals are believed to be involved. Further, the transgenic animals of this invention may be used to test medications and procedures to protect against ischemia-reperfusion injury due to reoxygenation. This type of injury occurs frequently in the heart, kidneys, and intestines.

In a more general manner, the transgenic mammals of the invention provide classic models to determine whether and how to prolong or influence their life spans or to attenuate the development of age-related diseases by modulating antioxidant enzye activities and/or whether the overexpression of antioxidant enzymes in mammals affect their sensitivity (or resistance) to a variety of stresses including oxidative stress. It is expected that the findings can be applied to humans and thus contribute to solving several health problems, whether attributable to aging or not.

Further objects and embodiments of the invention will become apparent from a consideration of the ensuing description and figures.

"Genotype" imeans the genetic constitution of an organism as distinguished from its physical appearance.

"Phenotype" means the observable properties of an organism as produced by the genotype in conjunction with the environment.

"Selectable phenotype" is a phenotype which confers upon an organism the abilihy to exist under conditions which kill off all organisms not possessing the phenotype. Examples include drug resistance, resistance to environmental conditions like temperature or an improved ability to withstand the effects of oxidative species.

DETAILED DESCRIPTION OF THE DRAWINGS

FIG. 1 is three diagrams showing the structure of human Cu,Zn SOD, GPP, and GPE transgenes with the HMGCR promoter. For construction of the transgenes, cDNA sequences of each of the human genes were inserted into unique BamHI sites of pHMG. The transgenic mice were generated with NotI DNA fragments of the plasmids.

Figure 2:
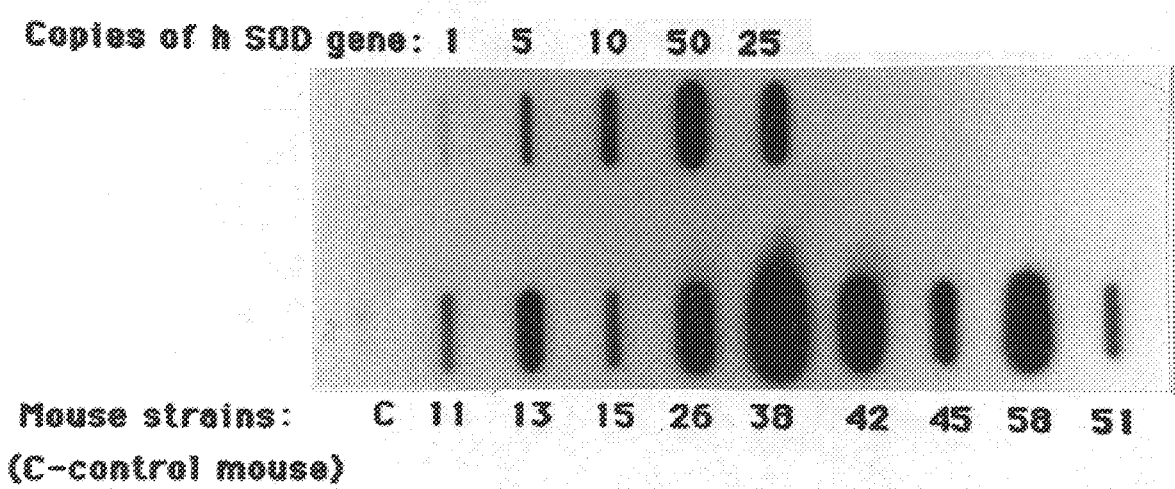
FIG. 2 is a slot-blot analysis of the human Cu,Zn SOD gene integrated in the mouse genome.

FIG. 2 is an estimation of copy number of human Cu,Zn SOD gene integrated into the mouse genome. Copy numbers varied from lower than one in mosaic mice to more than 100.

Figure 3A:
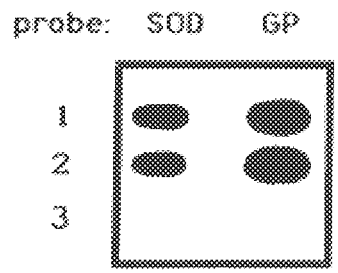
FIG. 3A is a Southern blot analysis of two transgenic mice expressing both hSOD and hGPE.
Figure 3B:
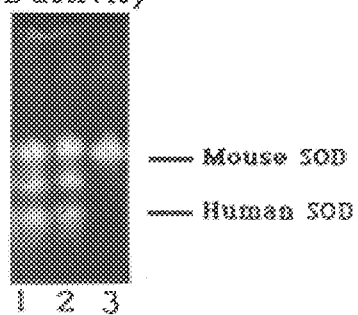
FIG. 3B is PAA gel of two transgenic mice expressing both hSOD and hGPE.

FIGS. 3A and 3B are an analysis of transgenic mice containing both human Cu,Zn SOD and human GPE. FIG. 3(A) is a Southern blot analysis of genomic DNA with labeled SOD and GPE probes, and FIG. 3(B) is an electrophoresis SOD enzyme assay of transgenic progeny. Lanes 1 and 2 of FIG. 3(B) are from progeny of mating SOD and GPE homozygotes. Lane 3 is a control mice containing neither of the human transgenes.

Figure 4A:
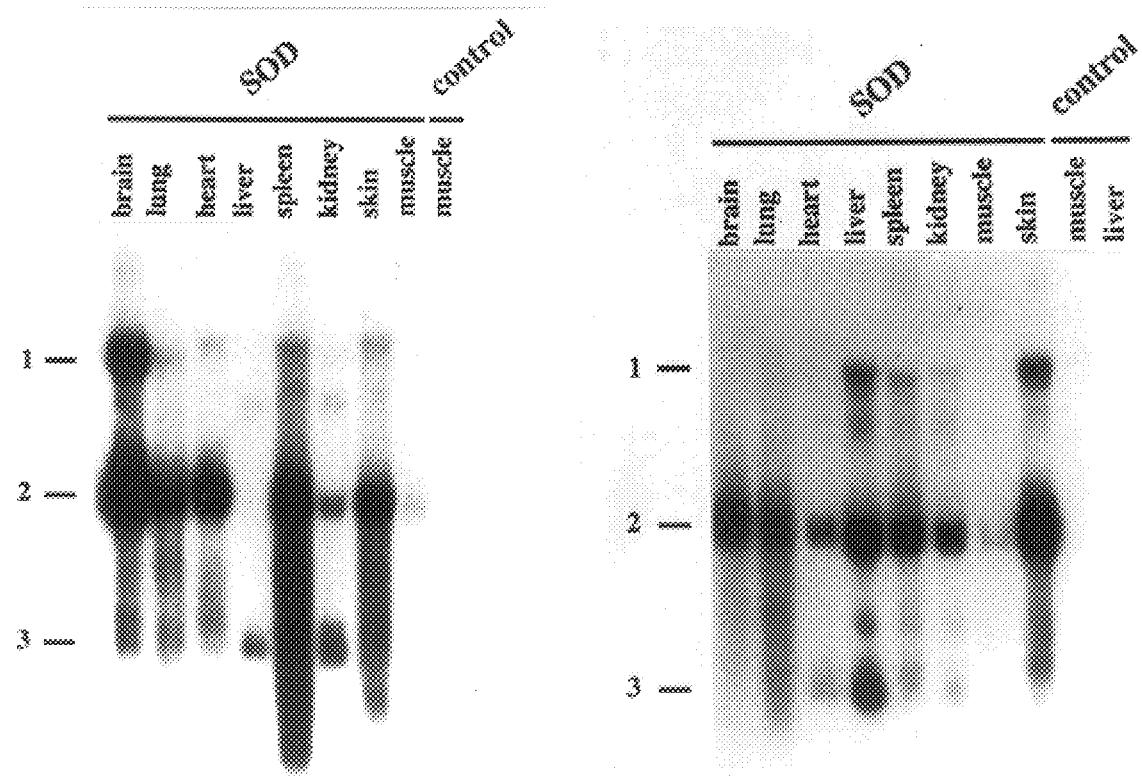
FIGS. 4A–4C are Northern blot analyses of various tissues F1 progeny of several transgenic mouse strains.
Figure 4B:
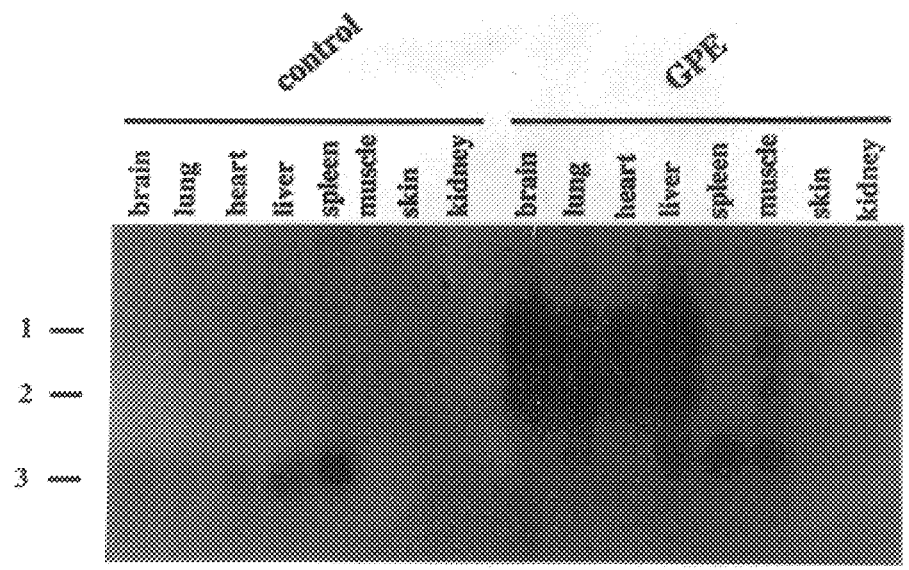
Figure 4C:
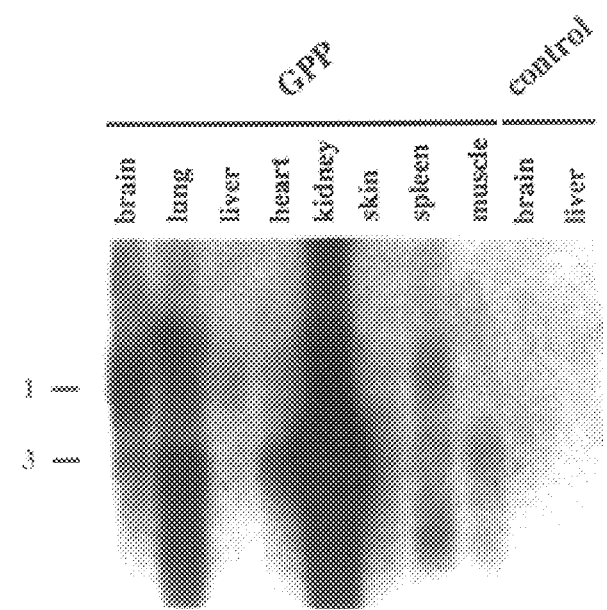
Figure 5B:
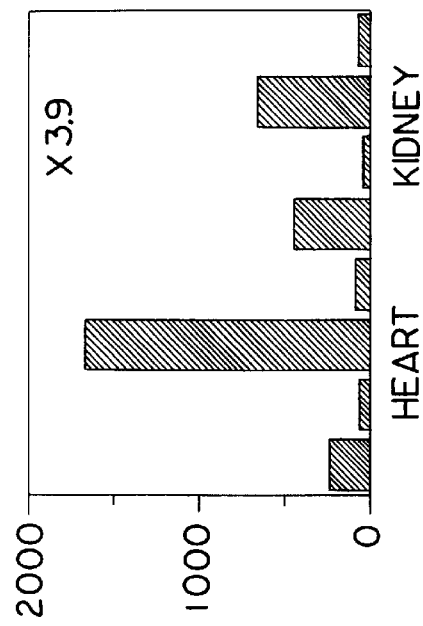
FIGS. 5A–5D are graphic depictions of the activity of tissues of transgenic mice as compared to normal littermates.
Figure 5D:
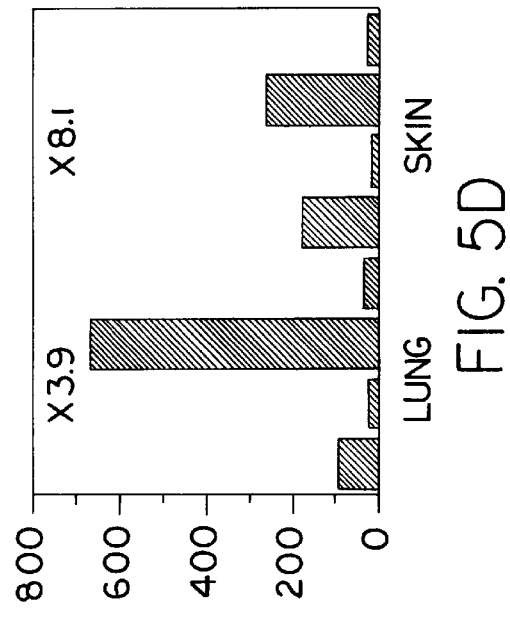
Figure 5A:
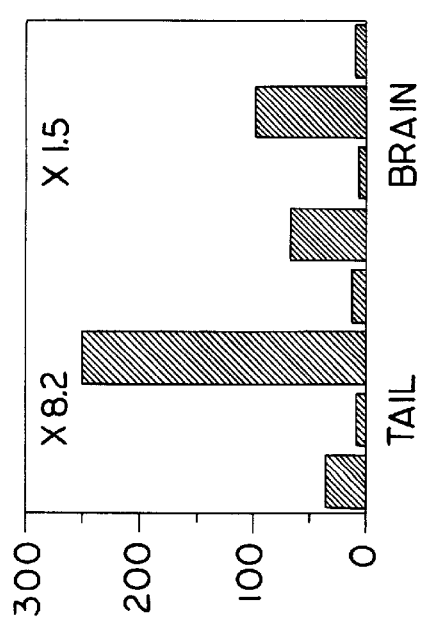
Figure 5C:
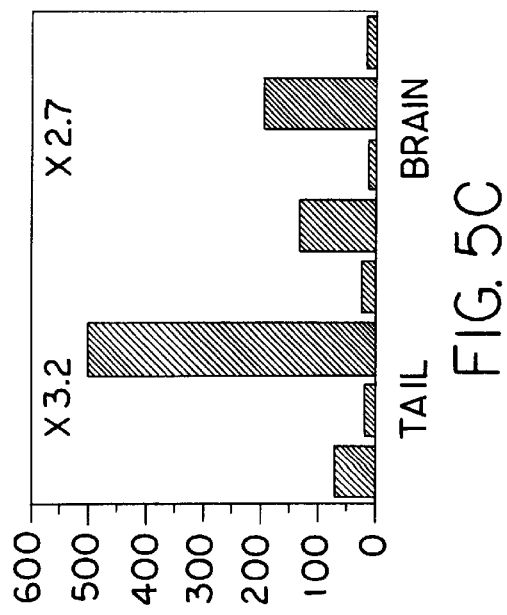

FIGS. 4A, 4B, and 4C are a Northern blot analysis of various tissues from the F1 progeny of several transgenic mouse strains. Bands 1 and 2 correspond to the mRNA of human transgenes. Band 3 corresponds to the mERNA from the murine SOD or GP genes. FIG. 4(A), (B), and (C) are Northern analyses of mice strains with SOD, GPE, and GPP, respectively, compared to control mice.

The transgenic mice express the transgenes in varying amounts in brain, lung, heart, liver, spleen, kidney, skin, and muscle. The controls showed no expression of human genes.

FIGS. 5A, 5B, 5C, and 5D graphically show the activity of superoxide dismutase in various tissues of control mice and in one strain of transgenic mouse with SOD. No correlation between the number of gene copies integrated and the level of gene expression was observed. The ratios of transgenic to control Cu,Zn SOD activity in a high expression strain was 1.5 for brain, 3.2 for liver, 3.9 for lung, 8.1 for skin, 3.9 for kidney, 2.7 for muscle, and 4.0 for spleen.

Figure 6:
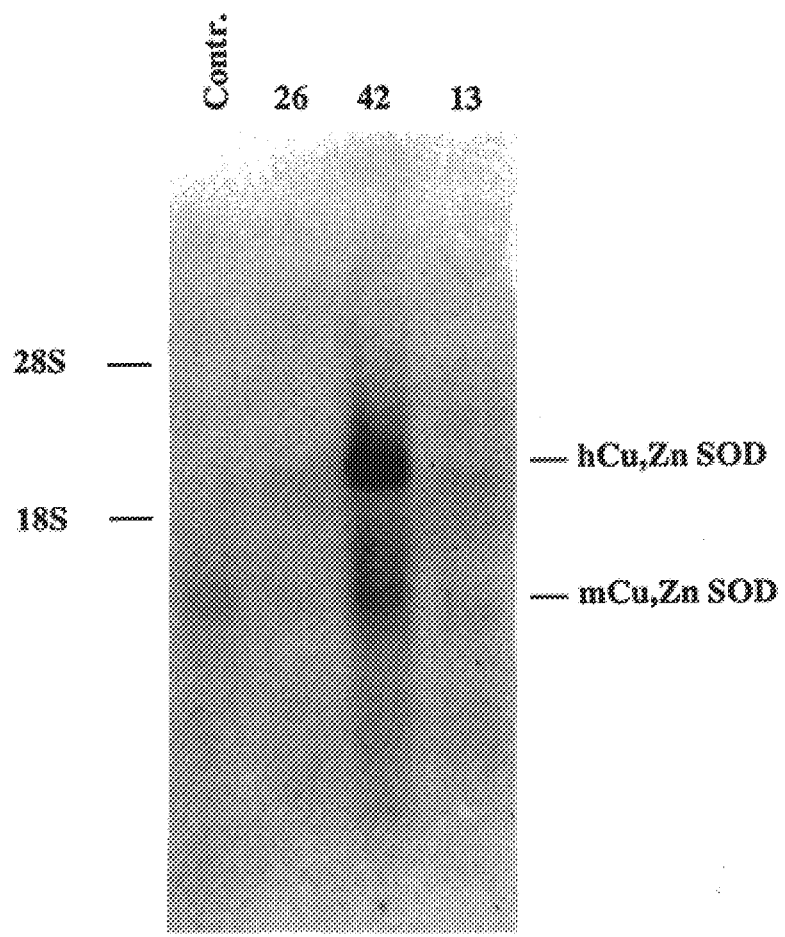
FIG. 6 is a Northern analysis of mRNA isolated from intraperitoneal macrophages of SOD transgenic mice, showing higher production of SOD in transgenic mice than in controls.

FIG. 6 is a Northern analysis of mRNA isolated from intraperitoneal macrophages of SOD transgenic mice. SOD activity was found to be 2.5 times higher in macrophages from heterozygous transgenic mice than in controls.

FIGS. 7A, 7B, 7C and 7D are a series of photomicrographs showing the cerebellar hemorrhage in brains of transgenic mice as compared to controls. 7(A) shows immunochemical localization of SOD in the cerebellum of SOD-transgenic mice. Staining was confined to the white matter tracts of the cerebellar peduncle and the cerebellar lobes. No staining was seen in a section of brain from control mice. 7(B) is a cerebellum from control mouse showing good preservation of white matter (W), granule cells (G), and molecular layers (M). 7(C) shows the fatal cerebellar hemorrhage following administration of 1,3-dinitrobenzene to SOD transgenic mice. Hemorrhage from the cerebellar vessels dissect the overlying molecular layers (M) and leptomeningeal coverings of the cerebellum. 7(D) shows the minimal areas of hemorrhage in a GPE mouse following administration of 1,3-dinitrobenzene.

Figure 8:
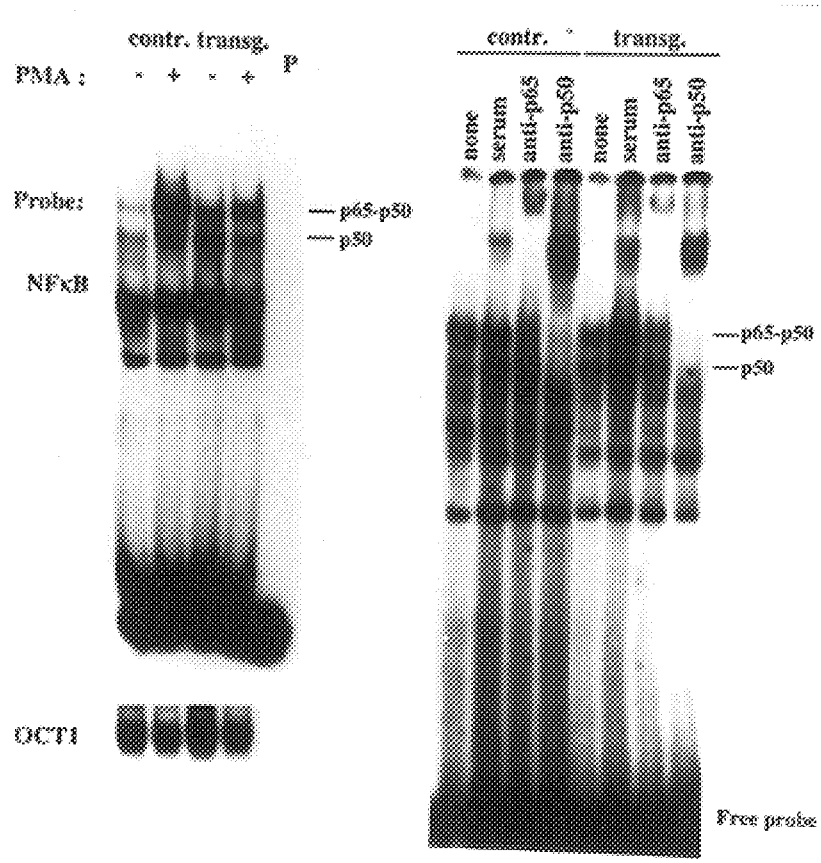
FIG. 8 is a supershift DBA for NF B probe and nuclear extracts from PMA treated macrophages indicating that signalling transduction pathways area are affected in hSOD transgenic mice.

FIG. 8 is a supershift DNA binding activity (DBA) analysis for NFκB, one of the most important transcription regulators in macrophages. The results of this analysis indicate that, in macrophages from transgenic mice with SOD, signalling transduction pathways are affected.

DETAILED DESCRIPTION OF THE INVENTION

The non-human animals of the invention have an immune system which includes non-specific phagocytes such as macrophages, and neutrophils. Such non-human animals include vertebrates like mammals such as rodents, non-human primates like monkeys such as baboons, chimpanzees, domestic animal species such as cows, sheep, dogs, cats, pigs, and reptiles, amphibians, and avian species. In a preferred embodiment of the invention, mice are used as the species into which the transgene is introduced, since mice are an accepted mammal model.

The method for producing the transgenic animals of the invention is carried out as follows.

The transgenic mice are produced by introducing transgenes into the germ line of the mouse. The transgene is injected into the male pronucleus of the fertilized egg. This results in all cells of the transgenic mouse carrying the incorporated transgene. In addition, 50% of the offspring of the founder mice will contain the transgene in their genome. The protocol further involves mating a transgenic mouse expressing the GP gene with a transgenic mouse expressing the SOD gene to produce a mouse carrying and expressing both genes and the progeny of these transgenes, both heterozygotes and homozygotes described herein. In the protocol, the following steps are followed:

a. providing a GPE, GPP, or SOD transgene. The SOD transgene is operably linked to a non-human, housekeeping promoter. In a preferred embodiment, the GPE and GPP transgenes may be operably linked to a non-human, housekeeping promoter which may be the same or different from that of the SOD transgene.

b. introducing the gene into the embryo of a non-human animal like a mouse.

c. transferring the embryo into a pseudopregnant animal of the same species, for example, a mouse.

d. allowing the embryo to develop to term.

In another embodiment, the following steps may be performed in addition to the above four steps.

e. identifying at least one transgenic offspring containing the transgene, and f. breeding the offspring to produce a transgenic mouse whose genome comprises and expresses the gene for SOD, GPE, or GPP. The transgenes of the transgenic mouse will correspond to the transgene that was introduced into the founder mouse embryo.

The invention is illustrated with select antioxidant enzymes, like the GPs and SOD. It is evident from the teaching herein that the invention is applicable to any antioxidant enzyme, and the gene thereof. Since this is an evolving field of research which is likely to be further stimulated by the publication or documentation or articles reporting this work, other antioxidant enzymes that are not yet identified or isolated, are considered with the scope of the invention.

Three major antioxidant enzymes are known: superoxide dismutase (SOD), catalase (CAT) and glutathione peroxidase (GP). Three forms of SOD are known in humans: homodimeric Cu,Zn SOD found mainly in the cytosol, homotetrameric glycosylated Cu,Zn SOD found in extracellular spaces, and homotetrameric MnSOD found mainly in mitochondria. CAT, a heme protein which has a single substrate—$H_2O_2$, is found in tissues mainly in peroxisomes and the cytosol. GP is a selenocysteine-containing enzyme and four different forms are known to be present in humans: the cellular GP (GP1 or GPE) located in cytosol and mitochondrial matrix, the plasma GP (GPP), and extracellular secretory enzyme, and the phospholipid hydroxyperoxide GP (GPPx), existing in both cytosolic and membrane bound forms. A fourth type-GPG1 has been isolated from liver cells. GP1 and GPPx are present in most of the tissues, while GPP is detected in plasma and human milk. In humans, GPP is expressed in liver, kidney, lung and heart, whereas in rodents GPP is expressed only in kidney.

Of the four known immunologically distinct hGP types, the plasma and the erythrocyte enzymes are present in highest quantities and are well known and have been sequenced. GPE is present in all mammals with the highest quantities found in the cytoplasm. GPP is also believed to occur in all species of mammals and has been found in the rabbit, rat, mouse, and bovine.

The gene for SOD has been isolated and characterized for several mammalian species, including human (Sherman et al), mouse (Benedetto et al), and rat (Ho and Crapo). In addition to these species, the amino acid sequence for equine (Lerch and Ammer), and bovine (Steinman et al) SOD has been characterized. The gene for GP from several species has been isolated and characterized, including human (U.S. Pat. No. 5,089,408, 1992), rabbit (Akasaka et al), rat (Ho et al), and mouse (Chambers et al). The above articles are incorporated herein expressly by reference. Other sequences of other genes may be known but not yet uncovered in a literature search.

The invention has been illustrated herein with the human SOD gene as disclosed in Sherman et al., *P.N.A.S.*, 80:5465–5469 (1983), the human GPP gene as disclosed in Takahashi et al., *J. Biochem.*, 108:145–148 (1990), and the human GPE gene as disclosed in Sukenega et al., *Nucd. Acids Res.*, 15(17):7178 (1987). These three articles are incorporated herein expressly by reference.

While a particular form of the human species of the GP (GPE and GPP) and SOD enzymes has been illustrated in the preferred embodiments of the invention, other human and non-human species of these enzymes, and the gene encoding the respective enzymes, are useful in accordance with the invention. The transgene of the invention may be derived from any mammalian species, such as humans (including primates like monkeys), mice, rats, rabbits, cows, and horses.

There is no apparent reason why one or more of the genes expressing an antioxidant enzyme would not perform in an equivalent or better manner than GP or SOD, illustrated herein. Also, it is within the scope of the invention to provide a transgenic animal carrying a multiplicity of antioxidant genes that will supplement and/or complement each other to attain the desired results. The selection of the combination of the genes will be determined by the nature of the biochemical reaction which is sought to be promoted or hindered (where a more limited amount of a reaction product is desirable) and the objective sought to be accomplished.

Nucleotide sequences that are not identical with the reported sequences encoding these enzymes because of the degeneracy of the genetic code or for other reasons (like genetic manipulation or synthesis of the sequences) are within the scope of the invention when they encode functionally substantially equivalent or equivalent enzymes, i.e., the enzymes catalyze the reactions herein discussed, for instance, in the case of GPP, the reduction of hydrogen peroxide and organic hydroxyperoxides by reduced glutathione.

One of the transgenes of a preferred embodiment of the invention is the human gene coding for Cu, Zn superoxide dismutase (hSOD). SOD is an enzyme which detoxifies reactive oxidative species (ROS) which are formed as a byproduct of aerobic life and are found in great quantities as byproduct of the body's non-specific defenses, including phagocytosis. SOD catalyzes the reaction whereby the superoxide anion, together with molecular oxygen and hydrogen cations are transformed into hydrogen peroxide and oxygen.

A second transgene of a preferred embodiment of this invention is that of human glutathione peroxidase (hGP). Two forms of this transgene are principally illustrated in the present invention, erythrocyte GP (hGPE) and plasma GP (hGPP). A third type of transgene is a double transgene, that of hSOD and hGPE or hGPP, as described herein after in greater detail.

A reason (but not the only one) for preferring the human genes (or their functional or immunological equivalent) is that when human applications of this invention are considered, it is expected that the human genes will be more acceptable. Thus, the studies involving this invention may be more meaningful for human application.

In accordance with the invention, a non-human promoter other than that for SOD or GP was linked to the transgenes of the invention. In the preferred embodiments, the promoter of mouse hydroxy-methylglutaryl coenzyme A reductase (HMGCR) was linked to SOD and GPE and GPP for introduction into the genome of the mice. HMGCR promotes a ubiquitous pattern of expression of the enzymes in all tissues.

To be expressed, the structural gene was operably linked to a promoter in a functional manner. The gene is generally under the control of a promoter sequence different from the promoter sequence controlling transcription of the endogenous coding sequence. The promoter may be an inducible promoter, preferably a housekeeping or constitutive promoter which may be of viral origin. Examples of such suitable promoters are those derived from mouse mamidary tumor virus (MMTV) and cytomegalovirus (CMV). The promoter may be a synthetic promoter, i.e., it may be man-made.

Using the pHMG plasmid, transgenic mice containing within their genome hSOD, hGPE, or hGPP under the HMGCR promoter, were generated. In addition, homozygotes with hSOD and homozygotes with hGPE were mated, producing heterozygous offsprings containing both human enzymes concurrently.

Double heterozygote transgenic mice, containing the human genes for SOD and for GP are constructed as follows:

Heterozygote founder animals are produced by recombinant methods as described above. A founder animal, designated as the $P_1$ generation, is mated with an offspring $F_1$ transgenic mouse of the opposite sex which is heterozygous for the SOD or GP transgene. Based on classical genetics, one fourth of the results of this backcross are homozygous for the transgene.

The above procedure is used to produce homozygous mice for each of SOD, GPP, and GPE transgenes.

The production of double heterozygous mice, following the above backcross, follows classical genetics. If it is desired to have 100% transmission of both SOD and GP genes, a homozygous SOD mouse is mated with a homozygous GP mouse of the opposite sex. If less than 100% double homozygous mice are desired, the following procedures can be employed.

Crossing homozygous SOD mice with heterozygous GP mice will result in 50% double heterozygotes and 50% heterozygous for SOD but lacking the GP transgene.

Crossing heterozygous SOD mice with homozygous GP mice will result in 50% double heterozygotes and 50% heterozygous for GP but lacking the SOD transgene.

Crossing heterozygous SOD mice with heterozygous GP mice will result in 25% double heterozygotes, 25% heterozygous for SOD but lacking GP, 25% lacking SOD but heterozygous for GP, and 25% control mice lacking SOD and GP.

The same protocol is followed to generate mice carrying the hSOD and hGPE genes.

The determination of whether a transgenic mouse is homozygous or heterozygous for the SOD gene and/or the GP gene is performed as follows:

An offspring of one of the above described breeding crosses is mated to a normal control non-transgenic animal. The offspring of this second mating are analyzed for the presence of the transgene by the methods described later. If all offspring of this cross test positive for the transgene, the mouse in question is homozygous for the transgene. If, on the other hand, some of the offspring test positive for the transgene and others test negative, the mouse in question is heterozygous for the transgene.

An alternative method for distinguishing between a transgenic animal which is heterozygous and one which is homozygous for the transgene is to measure the intensity with radioactive probes following Southern blot analysis of the DNA of the animal. Animals homozygous for the transgene would be expected to produce higher intensity than would heterozygote transgenic animals.

All transgenic mice with human SOD expressed the transgene. Similarly, all transgenic mice with the human GP gene expressed the transgene.

The transgenic mice of the invention showed several unexpected properties related to the overexpression of the transgenes, some of which are identified below:

Transgenic mice overexpressing SOD had increased susceptibility to tumor production following treatment with known tumor producing agents applied to the skin.

Transgenic mice overexpressing GP had increased susceptibility to toxicity following administration of acetaminophen.

Transgenic mice overexpressing SOD had increased susceptibility to dinitrobenzene induced brain damage.

Transgenic mice overexpressing GP had increased sensitivity to hyperthermia when compared to normal mice and to mice overexpressing SOD.

Transgenic mice overexpressing both GP and SOD had increased tolerance to hyperthermia.

Cellular and humoral immune responses are known to decline with age. The decline of the immune system with age may be attributed, at least in part, to the changing levels of antioxidant enzymes. A number of antioxidants have been shown to enhance both humoral and cellular immune responses indicating that some endogenous free radical reactions have adverse effects on the immune system. The immune system in the transgenic mice of the invention overproducing antioxidant enzymes was studied by examining the properties of the neutrophils and macrophages of the mice. It was found that the immune system of the mice was markedly affected.

To investigate ROS metabolism in SOD transgenic mice, neutrophils and intraperitoneal macrophages were isolated and $O_2^-$, $H_2O_2$, and $NO_2$ production in resting and induced cells was measured. $H_2O_2$ production was tested with 2',7'-dichlorofluorescein diacetate (DCHF-DA) as a fluorescent probe. Flow cytometry indicated that under the induction by 12-O-tetradecanoylphorbol-13-acetate (PMA) the induction of $H_2O_2$ was 2.3 times higher in macrophages and 8 times higher in neutrophils from transgenic mice as compared to the control mice.

Interestingly, activated macrophages from animals with the hSOD gene produced $O_2^-$ two times higher than normal mice. The overproduction of the oxygen radical is likely due to NADPH-oxidoreductase. This enzyme for some reason was indeed much more activated in the presence of elevated levels of SOD. Since superinduction of the hexose monophosphate shunt (HMPS) can be considered as source of the elevated level of NADPH, the substrate for NADPH oxidoreductase, HMPS activity was determined by measuring the $CO_2$ formation in intraperitoneal macrophages. Activity of HMPS was indeed two times higher in cells from transgenic animals than those from normal mice.

Nitric oxide production was also examined, since nitric oxide synthase is thought to be employed in mediating macrophage cytotoxic and bacteriocidal activity. Macrophages were induced by lipopolysaccharides (LPS) and LPS+ γINF and showed essentially lower nitrite production from transgenic mice in comparison to control.

To assess the influence of elevated Cu,Zn SOD activity on bacteriocidal activity, induced intraperitoneal macrophages from transgenic and normal mice were purified and tested for their ability to kill E. coli, K12 and Candida albicans cells. The most important microbiocidal activity of macrophages from transgenic animals was 2 to 3 fold less efficient. Experiments which tested DNA binding activity of NFκB, one of the most important transcription regulators in macrophages, suggest that signalling transduction pathways are also affected in macrophages from transgenic mice with SOD.

SOD can interfere with several regulatory mechanisms by generation of a potent nitrating agent, which modifies tyrosine residues of other proteins. To identify possible changes in efficiency of nitrotyrosine formation, macrophages from SOD transgenic and control mice were analyzed by in situ immunofluorescence western blotting with anti-nitrotyrosine antibodies. These results indicate a significantly higher presence of nitrotyrosine residues in macrophages from transgenic mice than from normal mice.

It is apparent from these studies that the control of ROS in a mammal like in a double transgene can result in beneficial effects on the immune system of the mammal.

The following additional examples represent a detailed description of the production of embodiments of the invention and the analysis of several characteristics of the transgenic animals of the invention. The following description is presented by way of example and is not to be construed as a limitation on the scope of the invention. All literature and other references referred to in this text and under "References" are expressly incorporated by reference.

EXAMPLE 1

Construction of the plasmid

For construction of the transgenes of this invention, the vector pHMG, containing the housekeeping gene promoter HMGCR, was used. cDNA sequences of human Cu,Zn SOD, erythrocyte and plasma GP genes were inserted into the unique BamHI site of pHMG. The structure of the plasmids are shown FIG. 1.

The plasmids with the promoter and the transgenes were cut at the 2 NotI sites to yield fragments containing the HMGCR promoter and one of the transgenes. These fragments were then inserted into the genome of mice.

EXAMPLE 2

Microinjection

C57BL/6xCBA/J hybrid eggs and CD1 eggs were used in the preferred mode. To super ovulate the egg donors, 8 to 12 week old females were injected with 0.1 ml of pregnant mare serum intraperitoneally at 50 units per ml in sterile PBS. Forty-five hours later, they were injected with 0.1 ml human chronic gonadotropin at 50 IU ml in water and mated individually with males. Cumulus masses from females with copulary plug were incubated in M2 medium with 50 ml of hyaluronidase (Sigma). Then the eggs were quickly transferred in M16 microdrop culture in 37° C. tissue culture incubator gassed with 5% $CO_2$.

Injection into the male pronucleus was performed by the technique of Hogan. For injection, the Nikon-Leitz microinjection apparatus was used. Eggs which survived microinjection were removed for transferring to pseudomothers, which were then examined on days 19 to 21 for delivery of live offspring.

DNA for microinjection was prepared as follows: prokaryotic cloning vector sequences were separated from the microinjected fragment by agarose gel electrophoresis, followed by purification of the DNA from the gel matrix using the glass powder procedure.

EXAMPLE 3

DNA Isolation and Analysis

DNA was isolated from tissues by the method of Murphy and Hanson. Powdered tissue was incubated in a buffer solution with 1% SDS and 100 micrograms per ml proteinase K at 50° C. overnight with subsequent extraction by phenol, phenol/chloroform and chloroform. The extract was precipitated. Transgenic animals were identified by restriction enzyme digestion of genomic DNA and Southern blot analysis. For this purpose, after 3 to 5 hours enzyme digestion, DNA fragments were separated on 1–1.2% agarose gel and, after denaturation, transferred to the Hybond N nylon membrane (Amersham) using Posiblot (Stratagene). To obtain radio labeled probes for DNA analysis, purified DNA fragments were labeled using Megaprime DNA labeling kit and alpha-$^{32}$P dCTP and dATP (Amersham) according to the manufacturer's protocol. Hybridization was conducted during 12 to 14 hours at 42° C. in a solution with 50% formamide according to the membrane manufacturer's instruction. After washing, the membranes were autoradiographed with intensifying screen.

For identification of transgenic progeny from founder mice, slot blot analysis in Minifold II slot-blot system (Schleisher and Schuell) were used. Ten micrograms of chromosomal DNA from the tail was denatured and applied to the manifold on Hybond N membrane. Hybridization was performed as described previously.

Fifteen percent of the transferred eggs produced babies after injection of the SOD gene. 10.5% of the transferred eggs gave babies after injection of the GPE gene and 8.4% after injection of the GPP gene. Of these, 32% contained SOD transgene, 26% contained GPE transgene and 20% contained GPP transgene. In general, efficiency of transgenic mice production with GP genes was lower than with the SOD gene. There was also lower survival rates after birth of transgenic mice with GP genes.

Copy numbers of the introduced genes varied from lower than 1 (mosaic mice) to more than 100 (founder 38) according to the comparative slot-blot analysis. See FIG. 2 and Table 1. Four founders (42, 45, 58, 81) revealed expression of human SOD in tail homogenates according to the electrophoresis enzyme assay. All transgenic founders were mated with normal mice for obtaining a progeny. Results of the analysis of the transgenes inheritance are shown in Table 2.

TABLE 1

A. Transgenic Mice with human Cu, Zn SOD gene

| Transgenic Founder | Sex | Approx. Copy Nos. of Genes | Enzyme Expression in Tail of Founder | Gene Delivery % | Enzyme Expression F1 Progeny | Homozygotes |
|---|---|---|---|---|---|---|
| 11 | M | <1 | − | 0 | − | − |
| 13 | F | ~30 | − | 55 | +[b] | + |
| 15 | F | <1 | − | 0 | − | − |
| 26 | M | ~60 | − | 45 | +[a] | + |
| 38 | M | >100 | − | 10 | +[b] (f2) | + |
| 42 | M | ~70 | + | 44 | +[b] | + |
| 45 | F | ~15 | + | 12 | +[b] (f2) | |
| 58 | M | ~70 | + | 12 | +[b] (f2) | − |
| 80 | F | <1 | − | | | |
| 81 | M | ~3 | + | 50 | + | − |

B. Transgenic Mice with human erythrocyte and plasma GP genes

| Gene | Transgenic Founder | Sex | Approx. Copy Nos. | Gene Delivery |
|---|---|---|---|---|
| plasma GP | 17 | M | ~10 | 45 |
| | 25 | M | ~25 | 60 |
| | 29 | F | ~45 | 39 |
| | 189 | F | ~34 | 48 |
| | 193 | F | <1 | 11 |
| | 195 | M | <1 | 14 |
| eryth. GP | 6 | M | ~5 | 14 |
| | 23 | F | ~45 | 50 |

[a]variable
[b]In all tested organs (brain, lung, kidney, heart, tail, skin, muscle, stomach)

TABLE 2

| Gene | Donor/ Pregnant | Eggs Collected/ Injected/ Transferred | Pups/ Live | Analyzed | Transgene/ Live |
|---|---|---|---|---|---|
| SOD | 56/51 | 910/772/518 | 78/68 | 65 | 11/10* |
| GPP | 25/25 | 535/452/410 | 60/47 | 57 | 9/6 |
| GP1 | 21/21 | 432/348/277 | 41/16 | 40 | 6/2 |

*Data shown in Table 2 were obtained using C57 BL/6 × CBA mice. One strain of SOD-transgenic mice was also constructed in CD-1 mice.

Four founders with SOD gene, one with GPE, and four with GPP genes delivered transgene to progeny with 38 to 60% efficiency. All positive mice in F1 progeny of SOD transgenic mice revealed transgene expression. Founders which delivered transgene to the progeny with efficiency most likely were mosaic.

Homozygous transgenic mice with SOD and GPE were produced using standard genetic breeding methods. Male and female heterozygous SOD transgenic mice were mated. Homozygous offspring were identified by DNA hybridization analysis as having twice the quantity of the transgene as contained in heterozygous transgenic mice. Alternatively, homozygous offspring can be determined by mating to non-transgenic mice. If the tested mouse is homozygous, all offspring of this mating will be SOD transgenic. Conversely, if not all of the offspring of the mating are SOD transgenic, the test mouse is not homozygous for the SOD transgene. The identical procedures can be used to produce and identify GP homozygous transgenic mice.

Homozygous mice with hSOD were then mated with homozygous mice with hGPE to produce heterozygous transgenic mice with both hSOD and hGPE. FIG. 3 shows a Southern blot analysis and enzyme assay of two of the transgenic mice expressing both hSOD and hGPE.

EXAMPLE 4

Expression of SOD and GP Transgenes

To obtain radio-labeled probes for RNA analysis, purified DNA fragments were labeled using the methods described above for producing probes for DNA analysis. RNA from various tissues was prepared by the modified guanidinium-thiocyanate extraction protocol. Poly A fraction of RNA was purified using oligo-dT Cellulose columns (Stratagene). Northern analysis was performed according to the method of Kroczek and Siebert. Ten micrograms of total cellular RNA or 3 micrograms of poly A mRNA prepared from tissues was denatured in 1×MOPS electrophoresis buffer, 6.54% formaldehyde, 50% formamide. RNA was loaded on submarine 1.2% to 1.4% agarose gel with 1.1% formaldehyde. RNA was separated for 4 to 5 hours. Following electrophoresis, the gel was blotted and hybridized as described above for Southern blot analysis.

Northern blot analysis of various tissues from the F1 progeny of the several transgenic mouse strains is shown in FIG. 4. High levels of messages for human genes were detected in most of the tissues in hSOD transgenic mice. The two strains presented with the highest level of expression differ in hSOD mRNA production in liver, kidney, skin, and muscle. There was also a relatively high level of unspliced mRNA in brain tissue of one mouse strain.

The level of expression of human GPE in one mouse strain was highest in brain, lung, heart, and liver tissues, and lower in muscle, skin, and kidney. A markedly high level of human GPP mRNA was observed in brain while much lower levels were detected in kidney, lung, and other tissues of a transgenic strain. No RNA for the human genes was detected in non-transgenic littermates.

EXAMPLE 5

Measurement of Activities of the Products of the Transgenes

Preparation of samples from tissues was performed as follows. Mice were anaesthetized by avertin and perfused by PBS. The organs were separated, weighed and homogenized by Tissumizer (Tekmar, Cincinnati). In 10–20 volume of 0.1M phosphate buffer (pH 7.8) containing 0.1 mM EDTA. The homogenates were centrifuged at 100,000 g for 30 minutes at 4° C. Cytosolic fraction was collected and kept at −70° C. until assayed. On the day of assay, the homogenates were filtered through a column with Sephadex G-10. Protein concentration was estimated by the method of Lowry.

Two methods were used for assessment of SOD activity. Tissue extract for the electrophoresis assay was loaded on a 10% polyacrylamide gel, containing 8M urea. Electrophoresis was performed for 3.5 hours in tris-glycine buffer (pH 8.0). SOD was localized by soaking the gel in solution of nitroblue-tetrazolium (2.5 mM) for 20 minutes followed by immersion for 20 minutes in a solution containing 28 mM TEMED, 0.3 $\mu$M riboflavin and 36 mM potassium phosphate (pH 7.8). Finally, the gel was illuminated for 15 minutes and photographed.

As a quantitative method, an indirect inhibition assay was used. The assay mixture contained 25 mM sodium phosphate (pH 7.8) 1.5 $\mu$m xanthine, 1 $\mu$mol hydroxylammonium chloride, 0.1 units per ml xanthine oxidase and the assay probe and total volume of 500 $\mu$l. In order to assay non Cu,Zn SOD activity, the assay mixture included 1 mM potassium cyanide. The mixture was incubated for 20 minutes, followed by addition of alpha-naphtolamine and sulfonic acid. The optical density was determined at 530 nm. One unit of enzyme corresponded to 50% inhibition of hydroxylammonium chloride oxidation.

GP activity was determined according to the method of Flohe and Guntser. Both sample and reference reaction mixtures contain 0.1M sodium phosphate buffer (pH 7.0), 0.5 mM EDTA, 0.2 mM NADPH, 1 U of glutathiione reductase, 1 mM sodium azide, 2 mM of reduced glutathione in 1 ml. The oxidation of NADPH by hydrogen peroxide (15 $\mu$m) added to the sample cuvette only, was followed at 340 nm at 37° C. One unit of enzyme activity was defined as the oxidation of 1 nmol of NADPH per minute.

Cu,Zn SOD and GP activities of the tissues of transgenic mice and their normal litter mates were measured and compared. See FIG. 5 and Table 3.

TABLE 3

| TISSUE | UNITS PER mg OF PROTEIN | | RATIO |
|---|---|---|---|
| | Control | Transgenic | (% to control) |
| Strain GPP-17 | | | |
| Lung | 0.560 | 0.620 | 110 |
| Brain | 0.075 | 0.083 | 111 |
| Kidney | 0.860 | 1.110 | 130 |
| Heart | 0.135 | 0.158 | 118 |
| Liver | 1.420 | 1.620 | 114 |
| Spleen | 0.520 | 0.510 | 098 |
| Skin | 0.019 | 0.027 | 145 |
| Blood | 0.440 | 0.680 | 155 |
| Strain GP1-23 | | | |
| Lung | 0.610 | 0.650 | 106 |
| Brain | 0.088 | 0.318 | 361 |

TABLE 3-continued

| TISSUE | UNITS PER mg OF PROTEIN | | RATIO |
|---|---|---|---|
| | Control | Transgenic | (% to control) |
| Kidney | 0.790 | 1.174 | 148 |
| Heart | 0.116 | 0.186 | 160 |
| Liver | 1.450 | 1.850 | 127 |
| Spleen | 0.440 | 0.640 | 145 |
| Skin | 0.022 | 0.046 | 209 |
| Blood | 0.640 | 0.600 | 094 |

No correlation between the number of gene copies integrated and the level of gene expression was observed. The ratios of transgenic to control SOD activity in heterozygotes of high expression strain was 1.5 for brain, 3.2 for liver, 3.9 for lung, 8.1 for skin, 3.9 for kidney, 2.7 for muscle and 4 for spleen. Transgenic mice with human plasma GP gene produced the highest level of GP activity in blood as was expected for this secreted form of GP.

In humans, the enzyme is usually detected in plasma and milk. mRNA synthesis was reported in liver, kidney, heart, lung and breast tissues of humans. However, in rodents it is not expressed in liver and it seems that the main secretory organ for plasma GP in these animals is kidney. The source of human plasma GP in blood of transgenic mice at this stage is not known although relatively high activity in the kidney was found. It is possible that the human enzyme in the transgenic mice undergoes the rodent's type of regulation. Differences in the patterns of expression detected by analysis of mRNA levels and the enzymes activity may be explained by complex regulation of selenocystine protein synthesis at the post-transcriptional level.

Better correlation between data of mRNA analysis and enzyme assays was found for transgenic mice with human erythrocyte GP (GPE). Overexpression of the enzyme activity was detected in all organs of a transgeilic mice strain, especially in brain, kidney, heart and skin.

EXAMPLE 6

Establishment of Cell Lines from Tissues of SOD, GPE, GPE/SOD Mice

In order to establish cell lines from tissues of transgenic and normal. mice, lung, kidney, muscle and mesenteric lymph nodes from SOD, GPE, SOD/GPE, and normal mice are removed aseptically, cut into very small pieces (1 mm$^3$) and put into a sterile tissue culture flask in a drop of medium. The flasks are then incubated at 37° C. until the tissue becomes attached to the surface of the flask. Explant outgrowth is seen in 1–2 weeks. Once a confluent monolayer is formed, cells are detached from the flasks. The cells can be frozen or can be passaged further.

EXAMPLE 7

Analysis of Properties of Intraperitoneal Macrophages and Neutrophils from Transgenic Mice with the SOD Transgene Resident macrophages from control and transgenic mice were washed from the peritoneal cavity without elicitation. Glycogen-elicited macrophages were obtained on the 4th day after intraperitoneal injection of a 0.5 ml of 2.5% glycogen solution. The exudate macrophages were centrifuged, washed, plated in growth medium and left for 2 h at 37° in a 5% $CO_2$ incubator. Nonadherent cells were removed by extensive washing and adherent cells received new medium with or without the inducer (LPS, PMA or ΓΝF). Quantiation of macrophage contents was done by differential staining (Diff-Quick, VWR) and latex bead phagocytosis. Neutrophils were obtained from heparinized venous blood and isolated by dextran sedimentation and centrifugation through Ficoll-Hypaque as described.

The expression of the SOD transgene was evaluated as to its effect on the function of intraperitoneal macrophages and neutrophils. In these mice, SOD activity assays indicated 2.5 higher production of SOD in macrophages from heterozygous transgenic mice compared to control mice. See FIG. 6.

The ability of macrophages to kill microorganisms was studied by coculturing macrophages with several dilutions of *E. coli*, K12, and *Candida albicans* at 37° in the presence of autologous serum. At different time points, aliquots of mixtures were removed and incubated with Na deoxycholate to lyse the cells.

For the *E. coli* assay, the aliquots were plated and quantity of bacteria were counted the next day. For the *Candida albicans* assay, 0.001% methylene blue solution was added to cell lysates.

After staining and washing, samples were used for the determination of surviving cells. It was found that the microbicidal activity of macrophages from transgenic animals was 2–3 fold less than that of control mice.

The $H_2O_2$-sensitive dye 2',7'-dichlorofluorescein diacetate (DCHF-DA), was used to measure peroxide production in neutrophils and macrophages. Cells were incubated for 15 min in the presence of dye and then stimulated by PMA for 20 min. Stained samples were analyzed using EPICS Profil flow cytometer (Coulter Electronics Inc.). The histogram generated in these experiments was analyzed using EPICS Cytologic Software. PMA induced production of $H_2O_2$ was 2.3 times higher in macrophages and 8 times higher in neutrophils as compared to the control mice.

For characteriLzation of nitric oxide synthase activity, nitrite/nitrate levels was determined after induction of macrophages by lipopolysaccharides (LPS) and LPS and γinterferon. Nitrite was measured in the cell-free supernatant by the Griess reagent, and nitrate was similarly assayed after reduction of nitrate to nitrite using nitrate reductase from Aspergillus niger. Treated macrophages showed 40–50% lower NO production in the transgenic mice than in controls.

Superoxide production was determined by the well established method using cytochrome C reduction at 550 nm. Activated macrophages from animals with the hSOD gene produced $O_2^-$ two times higher than control mice.

HMPS activity was determined by measuring the $CO_2$ formation in intraperitoneal macrophages. Cells were stimulated by PMA and incubated in medium containing 5.5 mM glucose and either $^{14}C_1$-glucose or $^{14}C_6$-glucose in air tight flasks. To stop the reaction, 50% trichloracetic acid was injected at various time points and the flask was then incubated for 1 h. Any $CO_2$ formed was trapped on a cotton swab soaked in NaOH which was counted in the scintillation counter. $^{14}CO_2$ formed by TCA activity ($^{14}C_6$) was subtracted from $^{14}C_2$ formed from $^{14}C_1$-glucose which allowed us to estimate HMPS activity. The HMPS activity was found to be two times higher in cells from transgenic mice than in controls.

For immunochemical staining, cells were cultured on 4-chamber glass slides and induced by PMA. Then cells were fixed in acetone and dried. The samples were immunostained with anti-nitrotyrosine polyclonal antibodies using Dado kit C and examined by microscopy. For quantitative analysis, whole protein cell lysates were prepared and used for amino acid analysis.

For preparation of nuclear extracts $5 \times 10^6$–$10^7$ cells were lysed in hypotonic buffer. Nuclei were washed and then extracted with buffer containing 0.4M NaCl and the extract was cleared by centrifugation. For DBA assay, the nuclear extracts were preincubated with poly dI/dC and 0–100 ng of nonradioactive competitive oligonucleotides on ice, after which double-stranded [$^{32}$P]-labelled oligonucleotide comprising NFkB binding site was added for further incubation. Nucleoprotein complexes were resolved by denaturing PAGE gel in 0.25×Tris-borate EDTA buffer and autoradiography. In order to identify various components of NFkB complexes, nuclear extracts were incubated with polyclonal antibodies against p50, p65 and c-Rel proteins. These mixtures were subjected to DBA as described above. See FIG. 8.

The above presented data demonstrate successful establishment of transgenic mice lines with elevated levels of Cu,Zn SOD, plasma and erythrocyte GP enzymes. Results on the characterization of oxygen radical metabolism and some defense properties of neutrophils and macrophages demonstrate that there are substantial changes in the function of the immune system of the transgenic animals. It is believed that these changes resemble the properties of immune systems of aged organisms, where imbalance of ROS synthesis and detoxification abilities of certain types of antioxidant enzymes may lead to the decline of immune system function. These transgenic mice are thus useful models to target processes or proteins which are very sensitive to changes in ROS production inside cells. Mice with both expressed enzymes hSOD and hGP (hGPE and/or hGPP) are powerful tools to modulate and control antioxidant enzymes.

EXAMPLE 8

Expression of Transgenes in Cell Culture

Cell lines established from transgenic mice are characterized in terms of the expression of the transgene message and their corresponding enzyme activities. Because the balance between several components of the antioxidant defense system is important for the cellular resistance to oxidative stress, the response of these cell lines overexpressing either GPE or SOD alone, or overexpressing both the genes simultaneously, to oxidative stress conditions generated by agents like $H_2O_2$, paraquat, menadione or the xanthine/xanthine oxidase system is evaluated. Cell lines derived from lung, muscle, mesenteric lymph node, or kidney of transgenic and nontransgenic mice are treated with different concentrations of oxidants, and DNA strand breakage, lipid peroxidation, protein oxidation and sensitivity to killing are determined.

Cell lines from normal and transgenic mice are subjected to sub-lethal concentrations of $H_2O_2$ and population doubling and activities of enzymes which decrease with age, such as ornithine decarboxylase and thymidine kinase, are evaluated. It is believed that cell lines with balanced overexpression of antioxidant genes may undergo a delay in aging due to oxidative damage.

EXAMPLE 9

Renal Reperfusion Injury in SOD Transgenic Mice

Reperfusion injury experiments were conducted by subjecting the mice (hSOD) to 45 minutes of renal ischemia followed by 24 hours of reperfusion. The animals were then sacrificed and tissue sections were examined. It was found that necrosis of the tubules at the corticomedullary junction was significantly less in the transgenic mice than in the controls. This result supports the hypothesis of the role of ROS in the induced damage from ischemia and reperfusion and the important protective role of SOD.

EXAMPLE 10

Acetaminophen Toxicity in GP Transgenic Mice

Three groups of mice (control, GPP and GPE transgenic mice) were given a toxic dose of acetaminophen of 375 mg/kg of body weight. Mice were sacrificed at 0, 4, and 24 hour time points. Total and oxidized glutathione was measured in the liver by the enzyme cycling method. Gross appearance of organs was noted and sections were examined for histopathology.

The acetaminophen overdose was most lethal in GPE mice, with 33% dying within 4 hours, and 66% dead by 24 hours. Reduced glutathione was decreased at 4 hours in control mice from 50% to 0% and in GPP mice from 63% to 38%. Histopathology studies on the mouse livers revealed negligible to mild necrosis in control mice at 4 hours and advanced necrosis at 24 hours. Transgenic mice displayed moderate necrosis at 24 hours and advanced necrosis at 24 hours.

These results demonstrate the important role of CP activity and the level of glutathione available for detoxification of acetaminophen. This system is an excellent model for the evaluation of aging, because glutathione deficiency is known to be a general property of aging tissues and the detoxification capacity of tissues declines with age. This system is not limited to acetaminophen. One skilled in the art will understand that other chemicals that cause depletion of glutathione or otherwise induce oxidative stress can be utilized in this manner in place of acetaminophen.

EXAMPLE 11

Dinitrobenzene Induced Encephalopathy (DNB) in SOD and GPE Transgenic Mice

Transgenic and control mice were injected with DNB. The mice were later sacrificed and their brains examined under light and electron microscopy. SOD Transgenic mice demonstrated massive cerebellar hemorrhage, much greater than in brains of injected controls and in brains of GP transgenic mice. See FIG. 7.

This data points out the role of ROS in DNB-induced encephalopathy, especially $H_2O_2$, which is overproduced in the brain of SOD transgenic mice. Benzene is a powerful industrial pollutant which affects workers exposed to the high levels of benzene. High benzene levels are common in, for example, auto and machine repair shops. Thus, because of the higher than normal susceptibility to benzene, the SOD transgenic mice of the invention are useful as a means of screening the work environment for unsafe levels of benzene.

Other aromatic compounds are expected to have a similar effect.

EXAMPLE 12

Increased Mutagenesis of SOD Transgenic Mice

In order to determine the increased rate of mutagenesis in SOD overexpressing mice and the protective effects of overexpression of GP, the genes for SOD and for GPE, linked operably to a housekeeping promoter are incorporated as described above into the genome of mice which contain a lacI (lac repressor) gene cloned into a λ shuttle vector incorporated into its genome (Big Blue™ Mouse Mutagenesis Assay System, Stratagene, Cincinnati, Ohio). Transgenic mice overexpressing SOD, GPE, and SOD and GPE are produced as described previously.

The transgenic mice and control mice are exposed to a known carcinogen by painting the carcinogen on the flipped skin surface of the mice or by exposing the mouse by the likely route of human exposure. Rate of mutagenesis is evaluated using the well established mutagenesis assay system of Kohler. Genomic DNA is isolated from the desired tissue of the mice and the λ vector is removed from the genomic DNA by mixing with an in vitro λ packaging extract. The phage is then used to infect a host *E. coli* strain which has a deleted lac region and contains a lacZ⁻ gene on a phi80 insert.

*E. coli* colonies containing a mutation that inactivates either the lac repressor protein or the lacI promoter or a mutation within the lac repressor binding domain which block repressor binding to the lacZ operator are detected as blue mutant plaques against a background of non-mutant colorless plaques.

Compared to control mice, increased amounts of mutagenesis occur when transgenic SOD mice are exposed to carcinogens which cause increases in the production of ROS. Protection from mutagenesis is observed in SOD/GP transgenic mice as decreased rates of mutagenesis occur compared to SOD transgenic mice. Even lower rates of mutagenesis occur in GP transgenic mice compared to SOD mice. The rate of mutagenesis in GP transgenic mice is observed to be lower than in control mice.

EXAMPLE 13

Increased Tumor Formation in SOD Transgenic Mice

The dorsal regions of 9 week old female normal and SOD transgenic mice were shaved with an electric clipper. Each of the SOD transgenic and normal populations was divided into two groups (10 per group), a treatment group and a control group. All mice were treated topically with 200 nmol DMBA (7,12-diinethylbenz[α]-antracene) in 200 μl acetone. The control group of mice received only acetone. After 1 week all mice were treated topically with 200 μl acetone, 5 nmol TPA (12-O-tetradecanoylphorbol-13-acetate) twice weekly for 20 weeks. Skin tumors >1 mM in diameter were counted and recorded over time for a period of 29 weeks.

All skin tumors were papillomas. After 29 weeks of experimentation both the quantity of tumors per mouse as well as the percentage of mice with tumors were higher in the transgenic mice. The results demonstrate that mice overproducing SOD in skin tissue are more susceptible to induced tumor formation.

EXAMPLE 14

Increased Sensitivity of GP Transgenic Mice to Hyperthermia and Double Transgenic Mice Hyperthermia was induced in transgenic mice with the GPP gene and with the GPE gene. The animals were placed in incubators at 38°, 40° and 42° C. Body temperatures ($T_c$) were continuously monitored by a rectal probe. Importantly, transgenic mice with both plasma and intracellular glutathione peroxidase genes survived significantly less time at elevated temperature. For example, survival time at 40° C. for control and SOD transgenic mice was 175 (S.E. ±7) and 165 (S.E. ±10) min respectively, whereas survival time for mice with plasma and erythrocyte glutathione peroxidase was 129 (S.E. ±3.9) and 96 (S.E. ±2.9) min, respectively. The same parameters at 38° and 42° C. produced similar patterns of survival, except that for all groups, the survival time increased correspondingly at 38° and decreased at 42°. $T_c$ values of normal mice rose continuously during heat exposure. But after a determined period $T_c$ stabilized itself and even slightly decreased.

Normal and SOD transgenic mice do not show a difference in their bodies' response and were able to keep this $T_c$ for a determined period of time, then it rose slowly and then the mice died. Mice with the GPE transgene raised their $T_c$ essentially the same as normal mice, then the $T_c$ increased and after a small drop, the mice died. Mice with the GPP transgene had the highest rate of $T_c$ increase in comparison to all tested groups of mice, but in contrast to the GPE mice, $T_c$ then stabilized. Exposure of normal and transgenic mice to 42° and 38° C. demonstrate essentially the same pattern of temperature dependence, except that all groups of mice reached end points faster at higher temperature and slower at lower temperatures.

Initial results of double transgenic mice (hGPE and hSOD) under comparative testing conditions showed increased resistance to hyperthermia as compared to the GPE transgenic mice. This suggests the protective effect of the SOD enzyme on the metabolism when GPE is overproduced. Similar effect can be predicted with GPP and SOD.

Histopathological examinations of section of the heart, lungs, liver, spleen, kidneys, and brain of the transgenic and normal mice immediately after dying after exposure to 40° C. indicate that mice exhibited acute pulmonary congestion, but demonstrated no overt pathology including necrosis. The sequential measurement of the rectal temperature clearly shows the cause of death was terminal lethal hyperthermia and mice overproducing glutathione peroxidases were essentially more sensitive to temperature induced hyperthermia. It is an acute physiologic death explaining why there was no detectable anatomic changes accountable for the demise. There was an initial state of adaption to the rise of environmental temperature followed by the abrupt terminal rise of the $T_c$ to a lethal level. Important, is that $T_c$ limit was different in control, SOD and GP mice.

EXAMPLE 15

The Role of the Transgenes of the Invention in Aging

A current theory of aging is that aging is due to accumulation of oxidative stress causing damage to macromolecules. As far as antioxidative enzymes can modulate the quantity of ROS found in tissues, transgenic mice with antioxidant genes represent an ideal model for investigating this aspect of aging.

SOD transgenic mice, as illustrated above, have increased levels of ROS, especially hydrogen peroxide. These mice are more susceptible than are GP transgenic mice to the minute, repeated damage of ROS to macromolecules that accumulates over time, resulting in aging changes. GP transgenic mice, however, may scavenge low levels of $H_2O_2$, which have negative effects on cellular defense mechanisms requiring $H_2O_2$ as a signalling molecule. Therefore, double transgenic mice, overproducing both SOD and GP, represent a more ideal model of aging than do either of the single transgenic mice.

To evaluate the role of the transgenes of this invention in aging, SOD transgenic mice, GP transgenic mice, double SOD and GP transgenic mice, and control non-transgenic mice are weaned at 21–28 days of age and housed individually in plastic cages on wood chip bedding. The mice are fed a purified diet (AIN93G) in an amount equal to 90% of the amount consumed ad libitum.

The mice are maintained in a microisolation housing cage barrier system to minimize the introduction of disease. To further control and monitor infectious diseases, serum samples from sentinel mice are tested against nine agent panels of common murine pathogens every six months for titers.

Room air temperature is maintained at 20°–24° C. and humidity at 40–70%. Room air ventilation, illumination and standard husbandry practices are provided to the animals in accordance with NIH (PHS) recommendations. Cages are assigned to specific positions on stainless steel standard racks in order to control for a shelf level and to prevent misidentification.

All mice are checked daily for any deaths and any mortality is recorded. Moribund mice and/or mice observed to be in significant pain or distress are euthanized. The mice are autopsied and any tissues appearing abnormal are fixed in buffered formalin. The samples are then studied histopathologically.

The median age of the tenth decile of survivorship of non-transgenic control mice is approximately 40 months. The life span of the transgenic mice overexpressing antioxidant enzymes (SOD, GPE, or SOD AND GPE) is to be studied over a four year period.

Several uses for the transgenic animals of the invention have been described. Additional uses and descriptions are provided.

The animals of the invention are useful to test a molecule suspected of inducing the formation of ROS, as follows. The animals are exposed to the molecule and the level of ROS in the animal's tissues is later determined and monitored. Chemicals which are known to induce the formation of ROS include benzidine, which induces depletion of GP in brain, acetaminiphen, which induces depletion of GP in liver, and benzene, which stimulates increased levels of SOD by stimulating differentiation and anaerobic metabolism of phagocytes resulting in enhanced levels of intracellular hydrogen peroxide.

Thus, the animals of the invention are useful to screen exposure to benzidine and benzene. The animals are exposed to an environment suspected of being contaminated with benzidine or benzene. Then, the levels of ROS are assayed from the tissues of the animals.

The mice of the invention are useful as models for diseases caused, at least in part, by an imbalance in ROS metabolism. These diseases include Alzheimer's disease, Downs syndrome, amyotrophic lateral sclerosis, Parkinson's disease, and other metabolic phenomena like aging.

Because glutathione deficiency is a general property of aging tissues, and detoxification capacity of tissues declines with age, the GPE transgenic mice with a decrease in liver glutathione levels and increased toxicity of acetaminophen are useful as a model for aging.

The mice of the invention are useful to test treatments designed to alleviate the diseases identified herein and published in scientific literature and to test treatments for inflammation, damage due to brain edema, and to pulmonary oxygen toxicity. In addition, the mice of the invention with the SOD gene are useful as models for ischemia-reperfusion myocardial injury due to reoxygenation following resumption of blood flow during open heart surgery.

The invention therefore provides reliable animal models for practical evaluation of molecules which may modulate immune deficiency measured by over-production or under-production based on an antioxidative enzyme (SOD and/or GP) of a mammal. The invention also provides models for screening molecules that induce free radical production in tissues or that are related to production of free radicals in mammal cells. Further, the animal models of the invention are useful for evaluation of disorders which are believed to be attributable to oxidative damage due to stress, such as heat and time. Another practical use is the evaluation of reperfusion damage to kidney and identification of molecules effective to minimize such damage.

The transgenic animals of the invention are also useful as a source of cells for cell culture. Cells carrying the transgenes can be cultured, using standard cell culture techniques.

An important use for the transgenic animals of the invention is as a model for hyperthermic injury to cancer cells. A general property of cancer cells is their increased susceptibility to heat induced damage compared with that of normal cells. It is hypothesized that this increase susceptibility may be related to the levels of ROS in cancer cells. Cancer cells subjected to increased temperature are also more susceptible to various anti-cancer agents. The mice of the invention with increased susceptibility to hyperthermia can be used to test various anti-cancer therapies designed to potentiate the effect of hyperthermia in those cells.

Although the present disclosure describes the invention, the publications cited herein may be of assistance in further understanding the invention. All literature references and patents identified herein are expressly incorporated by reference.

The following patents have been noted, U.S. Pat. Nos. 5,281,521, Trojanowski, et al. (1994); 5,179,017, Axel, et al. (1993); 5,182,196, Allet, et al. (1993); 5,183,949, Kindt, et al. (1993); 5,190,931, Inouye (1993); 5,223,610, Burton, et al. (1993); 5,221,778, Byrne, et al. (1993); 5,225,546, Dryja, et al. (1993); 5,270,191, McKay, et al. (1993); 5,089,408, Akasaka, et al. (1992); 5,162,215, Bosselman, et al. (1992); 5,175,383, Leder, et al. (1992); 5,175,384, Krimpenfort, et al. (1992); 5,175,385, Wagner, et al. (1992); 4,736,866, Leder, et al. (1988); EPO Publication No. 89 306071.5 (1993); and PCT Publication No. WO 88 00835 (1987).

It will be appreciated by those ordinarily skilled in the art that the present specification and examples are set forth by way of illustration only and not limitation, and that various modifications and changes, especially those that bring about substantially same results, may be made without departing from the spirit and scope of the invention.

REFERENCES

1. Aceto, A., et al., "Effect of Ischaemia-Reperfusion on Glutathione Peroxidase, Glutathione Reductase and Glutathione Transferase Activities in Human Heart Protected by Hypothermic Cardioplegia", Free Rad. Res. Comms., 8(2):85–91 (1990)
2. Akasaka, M., Mizoguch, J., Yoshimura, S., and Watanabe, K., "Nucleotide sequence of cDNA for rabbit glutathione peroxidase", 17(5):2136 (1989)
3. Amstad, P., Moret, R., Cerutti, P., "Glutathione Peroxidase Compensates for the Hypersensitivity of Cu,Zn-Superoxide Dismutase Overproducers to Oxidant Stress", The Journal of Biological Chemistry, Vol. 269, No. 3, Issue of Jan. 23, pp. 1606–1609, 1994
4. Avraham, K. B., et al., "Down's Syndrome: Abnormal Neuromuscular Junction in Tongue of Transgenic Mice with Elevated Levels of Human Cu/Zn-Superoxide Dismutase", Cell, 54:823–829 (1988)
5. Benedetto, M. T., Yuzuru, A., and Gordon, J. W., "Isolation and analysis of the mouse genomic sequence encoding $Cu^{2+}$-$Zn^{2+}$ superoxide dismutase, Gene, 99:191–194 (1991)
6. Benzi, G., Pastoris, O., and Villa, R. F., "Changes Induced by Aging and Drug Treatment of Cerebral Enzymatic Antioxidant System", Neurochem. Res. 13:467–478 (1988)
7. Benzi, G., Pastoris, O., and Villa, R. F., "Changes Induced by Aging and Drug Treatment of Cerebral Enzymatic Antioxidant System", Neurochem. Res. 13:467–478 (1988)
8. Bewley, G. C., "cDNA and deduced amino acid sequence of murine Cu—Zn superoxide dismutase", Nucleic Acids Research, 16(6):2728 (1988)
9. Big Blue™ Mouse Mutagenesis Assay System, Stratagene, Cincinnati, Ohio
10. Buckman, T. D., Sutphin, M. S., and Mitrovic B., "Oxidative Stress in a Clonal Cell Line of Neuronal Origin: Effects of Antioxidant Enzyme Modulation", J. of Neurochem., 60(6):2046–2058 (1993)
11. Burk, Raymond F., "Molecular Biology of Selenium with Implications for its Metabolism", The FASEB Journal, 5:2274–5394 2279 (1991)
12. Cand, F., and Verdetti, J., "Superoxide Dismutase, Glutathione Peroxidase, Catalase, and Lipid Peroxidation in the Major Organs of the Aging Rats", Free Radical Biol. Med. 7:59–63 (1989)
13. Ceballos, I., et aL., "Expression of Human Cu—Zn superoxide dismutase gene in transgenic mice: Model for Gene dosage effect in down syndrome", Free Rad. Res. Commis., Vols. 12–13, pp. 581–589 (1991)
14. Ceballos-Picot, I., et al., "Age-related changes in antioxidant enzymes and lipid peroxidation in brains of control and transgenic mice overexpressing copper-zinc superoxide dismutase", Mutation Research, 275:281–293 (1992) Cerutti, P. A. and Trump, Benjamin F., "Inflammation and Oxidative Stress in Carcinogenesis", Cancer Cells, 3(1):1–7 (1991)
16. Chambers, I., Frampton, J., Goldfarb, P., Affara, N., McBain, W., and Harrison, Paul R., "The structure of the mouse glutathione peroxidase gene: the selenocystein in the active site is encoded by the 'termination' codon, TGA", The EMBO Journal, 5(6):1221–1227 (1986)
17. Chan, P. H., et al., "Cold-induced Brain Edema and Infarction are Reduced in Transgenic Mice Overexpressing CuZn-Superoxide Dismutase", Annals. of Neurology, 29(5):482–487 (1991)
18. Chen, T., Richi, J. P. Jr., Lang, C. A., "Life Span Profiles of Glutathione and Acetaminophen Detoxification", Drug Metabolism and Dispositions, 18(6):882–887
19. Chu, F. F., Doroshow, J. H., Esworthy, R. S., The Journal of Biological Chemistry, 268(4):2571–2576 (Feb. 5, 1993)
20. Damier, P., et al. "Glutathione Peroxidase, Glial Cells and Parkinson's Disease", Neuroscience, Vol. 52, No. 1, pp. 1–6 (1993) (Accepted August, 1992)
21. Epstein, Charles J., et al., "Transgenic mice with increased Cu/Zn-superoxide dismutase activity: Animal model of dosage effects in Down syndrome", Proc. Natl. Acad. Sci. USA, 84:8044–8048 (1987)

22. Gautier, C., Mehtali, M., and Lathe, R., "A ubiquitous mammalian expression vector, pHMGC based on a housekeeping gene promoter", *Nucleic Acids Research*, 17(20):8389 (1989)
23. Grove, Matthew and Plumb, Mark, "C/EBP, NF-κB, and c-Ets Family Members and Transcriptional Regulation of the Cell-Specific and Inducible Macrophage Inflammatory Protein 1α Immediate-Early Gene", *Molecular and Cellular Biology*, p. 5276–5289, September 1993
24. Halliwell, B. and Gutteridge, J. M. C., "Role of Free Radicals and Catalytic Metal Ions in Human Disease: An Overview", *Methods in Enzymology*, 186:1–85
25. Harris, Edward D., "Regulation of Antioxidant Enzymes", *The FASEB Journal*, 6:2675–2683 (1992)
26. Healy, A. M., Mariethoz, E., Pizurki, L. and Polla, B. S., "Heat Shock Proteins in Cellular Defense Mechanisms and Immunity", *Annals New York Academy of Sciences*, 663:319–330
27. Ho, Y. S., Howard, A. J., and Crapo, J. D., "Nucleotide sequence of a rat glutathione peroxidase cDNA", *Nucleic Acid Research*, 16(11):5207 (1988)
28. Ho, Y. S., and Crapo, J. D., "cDNA and deduced amino acid sequence of rat copper-zinc-containing superoxide dismutase", *Nucleic Acid Research*, 15(16):6746 (1987)
29. Jaffe, E. K., Abrams, W. R., Kaempfen, H. X., and Harris, K. A. Jr., "5-Chlorolevulinate Modification of Porphobilinogen Synthase Identifies a Potential Role for the Catalytic Zinc", *Biochemistry*, 31:2113–2123 (1992)
30. Kolb, E., Laine, E., Strehler, D., and Staehel, P., "Resistance to Influenza virus Infection of mx Transgenic Mice Expressing Mx Protein under the Control of Two Constitutive Promoters", *Journal of Virology*, p. 1709–1716, March 1992
31. Lerch, Konrad and Ammer, Doris, "Amino Acid Sequence of Copper-Zinc Superoxide Dismutase from Horse Liver", *The Journal of Biological Chemistry*, 256(22):11545–11551 (1981)
32. Lopez-Torres, M., Perez-Campo, R., Rojas, C., Cadenas, S., and Barja, G., "Simultaneous Induction of SOD, Glutathione Reductase, GSH, and Ascorbate in Liver and Kidney Correlates with Survival During Aging", *Free Radical Biol. & Med.* 15:133–142 (Received 21 May 1992; Revised 3 Feb. 1993; Accepted 24 Feb. 1993)
33. Mirault, M. E., Tremblay, A., Beaudoin, N., and Tremblay M., "Overexpression of Seleno-glutathione Peroxidase by Gene Transfer Enhances the Resistance of T47D Human Breast Cells to Clastogenic Oxidants", *The Journal of Biological Chemistry*, 266(31):20752–20760 (1991)
34. Mirault, M. E., Tremblay, A., Trepanier, G., Furling, D., and Puymirat, J., "Transgenic Mice Overexpressing Se Glutathione Peroxidase in the Brain: Differential Resistance to MPTP Mediated Neurotoxicity", *J. Cellular Biochem.*, Keystone Symposia on Molecular and Cellular Biology, Supp. 17, "Molecular Biology of Aging", page 168 (1993).
35. Mitchell, J. R., M.D., Ph.D., "Acetaminophen Toxicity" *New England Journal of Medicine*, Editorial, Vol. 319, No. 24, pp. 1601–1602 (1988)
36. Mullenbach, G. T., Tabrizi, A., Irvine, B. D., Bell, G. I., and Hallewell, R. A., "Sequence of a cDNA coding for human glutathione peroxidase confirms TGA encodes active site selenocystein", *Nucleic Acid Research*, 15(13):5484 (1987)
37. Orr, W. C., and Sohal, R. S., "The Effects of Catalase Gene Overexpression on Life Span and Resistance to Oxidative Stress in Transgenic Drosophila melanogaster", *Arch. Biochem, Biophys.* 297:35–41 (1992)
38. Oury, T. D., et al., "Cold-induced Brain Edema in Mice", *The Journal of Biological Chemistry*, Vol. 268, No. 21, Issue of Jul. 25, pp. 15394–15398 (1993)
39. Rosen, D. R., et al., "Mutations in Cu/Zn superoxide dismutase gene are associated with familial amyotrophic lateral sclerosis", *Letters to Nature*, 362:59–62 (Mar. 4, 1993)
40. Rusting, Ricki L., "Trends in Biology: Why do we age?", *Scientific American*, 131–141 (December 1992)
41. Sherman, L., Dafni, N., Lieman-Hurwitz, J., and Groner, Y., "Nucleotide sequence and expression of human chromosome 21-encoded superoxide dismutase mRNA", *Proc. Natl. Acad. Sci. USA*, 80:5465–5469 (1983)
42. Sohal, R. S., Sohal, B. H., and Brunk, U. T., "Relationship Between Antioxidant Defenses and Longevity in Different Mammalian Species" *Mech. Aging Dev.* 53:217–227 (1990)
43. Steinman, H. M., Naik, V. R., Abernethy, J. L., and Hill, R. L., "Bovine Erythrocyte Superoxide Dismutase", *The Journal of Biological Chemistry*, 249(22):7326–7333 (1974)
44. Sukenaga, Y., Ishida, K., Takeda, T., and Takagi, K., "cDNA sequence coding for human glutathione peroxidase", *Nucleic Acids Research*, 15(17):7178 (1987)
45. Sullivan, N., Gatehouse, D., Tweats, D., "Mutation, cancer and transgenic models: relevance to toxicology industry", *Mutagenesis*, (1993)
46. Takahashi, K., Avissar, N., Whitin, J., Cohen, H., "Purification and Characterization of Human Plasma Glutathione Peroxidase: A Selenoglycoprotein Distinct from the Known Cellular Enzyme", *Archives of Biochemistry and Biophysics*, 256(2):667–686 (1987)
47. Takahashi, K., Akasaka, M., Yamamoto, Y., Kobayashi, C., Mizoguchi, J., and Koyama, Jiro, "Primary Structure of Human Plasma Glutathione Peroxidase Deduced from cDNA Sequences", *J. Biochem.*, 108:145–148 (1990)
48. Tayarani, I. Cloez, I, Clement, M., and Bourre, J. M., "Antioxidant Enzymes and Reiated Trace Elements in Aging Brain Capillaries and Choroid Plexus", *J. Neurochem.* 53:817–824 (1989)
49. Tayarani, I., Cloez, I., Clement, M., and Bourre, J. M., "Antioxidant Enzymes and Related Trace Elements in Aging Brain Capillaries and Choroid Plexus", *J. Neurochem.* 53:817–824 (1989)
50. Toussaint, O., Houbion, A., and Remacle, J., "Relationship between the Critical level of Oxidative Stresses and the Glutathione Peroxidase Activity," *Toxicoloqy*, 81:89–101
51. White, Carl W., "Transgenic Mice with Expression of Elevated 1Levels of Copper-zinc Superoxide Dismutase in the Lungs are Resistant to Pulmonary Oxygen Toxicity", *The American Society for Clinical Investigation, Inc.*, 87:2162–2168 (1991)
52. Yarom, R., Sapoznikov, D., Havivi, Y., Avraham, K. B., Shickler, M., and Groner, Y., "Premature Aging Changes in Neuromuscular Junctions of Transgenic Mice with an Extra human CuZn-SOD Gene: A Model for Tongue Pathology in Down's Syndrome", *J. Neurol. Sci.* 88:41–53 (1988)

What is claimed:

1. A transgenic mouse whose somatic cells comprise and overexpress a transgene coding for glutathione peroxidase (GP) wherein the total native and transgenic GP expressed in the transgenic mouse is higher than the GP expressed in a non-transgenic mouse, which transgenic mouse has a phenotype of increased sensitivity to hyperthermia which is a decreased survival time due to the overexpression of the transgene.

2. The mouse of claim 1 wherein the GP transgene is human GP (hGP).

3. The mouse of claim 2 wherein the hGP transgene is human erythrocyte GP (hGPE).

4. The mouse of claim 2 wherein the hGP transgene is human plasma GP (hGPP).

5. The mouse of claim 2 wherein the transgene is under the control of a promoter other than that for hGP.

6. The mouse of claim 5 wherein the promoter is a housekeeping promoter from a non-human species.

7. The mouise of claim 6 wherein the promoter is the promoter for murine hydroxy-methylglutaryl-Coenzyrme A reductase (mHMGCR).

8. A transgenic mouse whose somatic cells comprise and overexpress ubiquitously in all tissues a transgene coding for glutathione peroxidase (GP) wherein the total native and transgenic GP expressed in the transgenic mouse is higher than the GP expressed in a non-transgenic mouse, which transgenic mouse has a phenotype of increased sensitivity to hyperthermia which is a decreased survival time as a result of overexpression of the transgene.

9. The transgenic mouse of claim 8 wherein the GP transgene is operably linked to mHMGCR.

* * * * *